United States Patent

Yoshihara et al.

[11] Patent Number: 5,836,941
[45] Date of Patent: Nov. 17, 1998

[54] LASER PROBE

[75] Inventors: Masaya Yoshihara; Masahiko Iida, both of Tokyo, Japan

[73] Assignee: Olympus Optical Co., Ltd., Tokyo, Japan

[21] Appl. No.: 653,069

[22] Filed: May 31, 1996

Related U.S. Application Data

[63] Continuation of Ser. No. 297,803, Aug. 30, 1994, abandoned.

[30] Foreign Application Priority Data

| Sep. 7, 1993 | [JP] | Japan | 5-222409 |
| Nov. 1, 1993 | [JP] | Japan | 5-273635 |
| Jun. 20, 1994 | [JP] | Japan | 6-137154 |

[51] Int. Cl.⁶ ............................................. A61B 17/36
[52] U.S. Cl. .......................... 606/15; 606/17; 600/108
[58] Field of Search ............................. 606/7, 13–17; 607/88, 89; 604/21, 22; 600/108

[56] References Cited

U.S. PATENT DOCUMENTS

| 4,669,467 | 6/1987 | Willett et al. | 606/17 |
| 4,740,047 | 4/1988 | Abe et al. | |
| 4,959,063 | 9/1990 | Kojima | 606/15 |
| 5,129,896 | 7/1992 | Hasson | 606/15 |
| 5,163,935 | 11/1992 | Black et al. | 606/17 |
| 5,242,438 | 9/1993 | Saadatnanesh et al. | 606/17 |
| 5,312,399 | 5/1994 | Hakky et al. | 606/15 |
| 5,320,617 | 6/1994 | Leach | 606/15 |
| 5,354,294 | 10/1994 | Chou | 606/17 |
| 5,366,456 | 11/1994 | Rink et al. | 606/17 |
| 5,496,307 | 3/1996 | Daikuzono | 606/15 |

FOREIGN PATENT DOCUMENTS

| 0463363 | 1/1992 | European Pat. Off. | 606/15 |
| 2681522 | 9/1991 | France | 606/17 |
| 2945080 | 5/1981 | Germany | 606/15 |
| WO 93/03678 | 3/1993 | WIPO . | |
| WO 93/12728 | 8/1993 | WIPO . | |

*Primary Examiner*—Michael Peffley
*Attorney, Agent, or Firm*—Frishauf, Holtz, Goodman, Langer & Chick

[57] ABSTRACT

A laser probe including an optical fiber for guiding a laser beam, a holder fixed at an end portion of the optical fiber, and a reflection tip detachably attached to the holder and having a reflection surface for reflecting the laser beam emitted from the optical fiber.

39 Claims, 12 Drawing Sheets

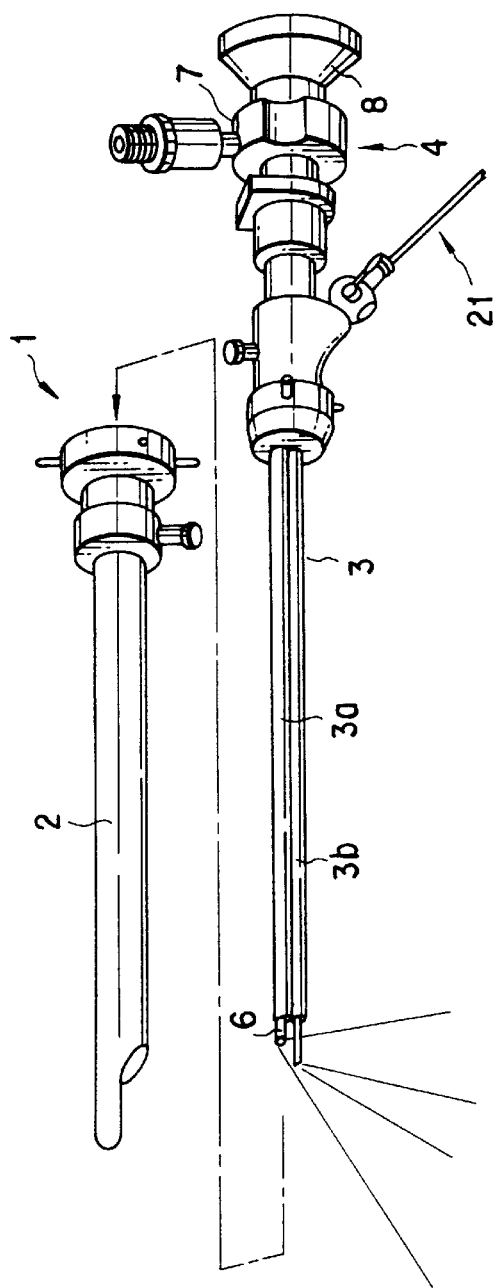
F I G. 4
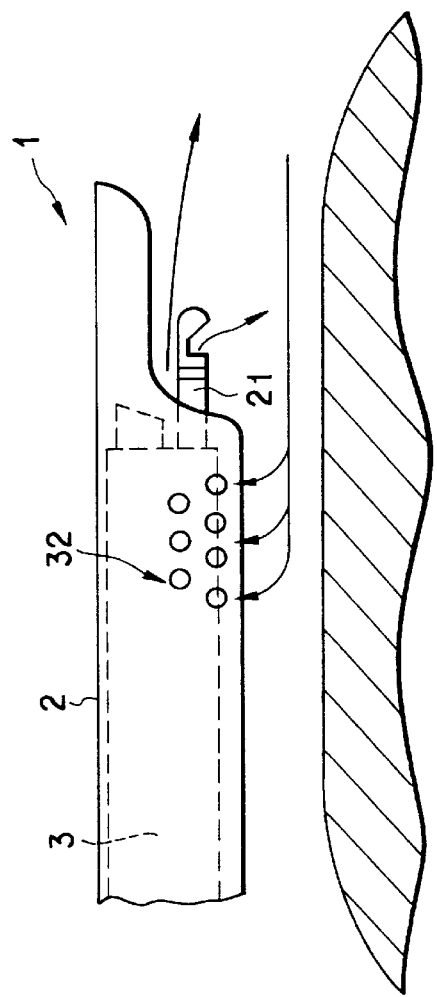
F I G. 5

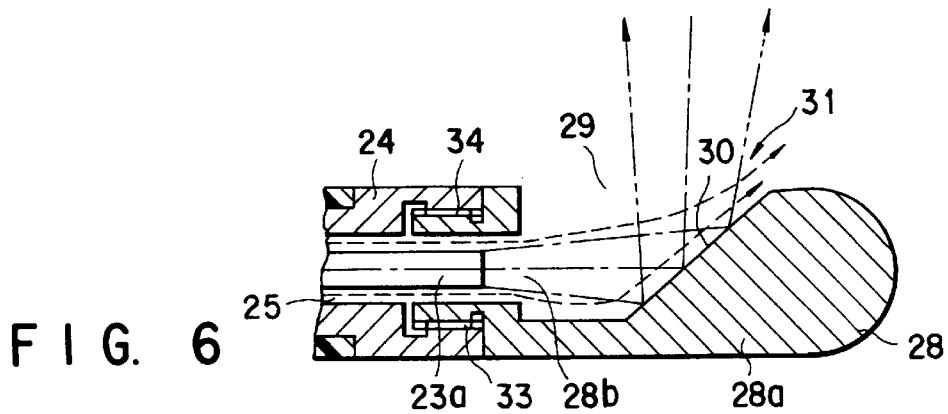
F I G. 6
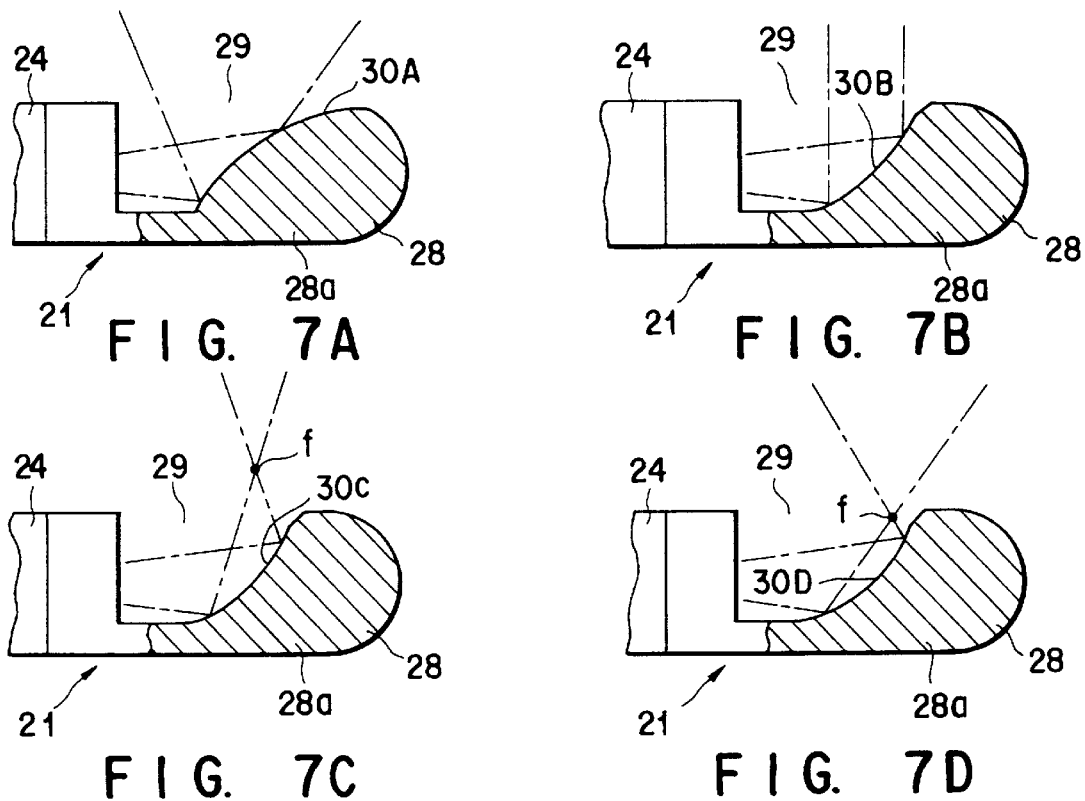
F I G. 7A  F I G. 7B
F I G. 7C  F I G. 7D
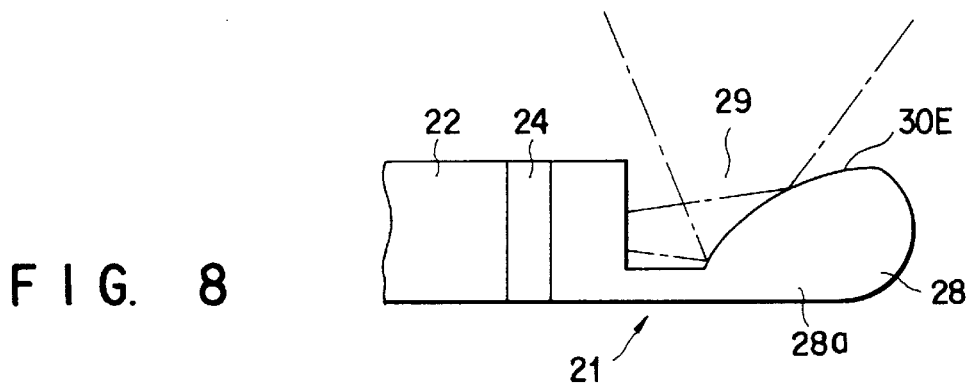
F I G. 8

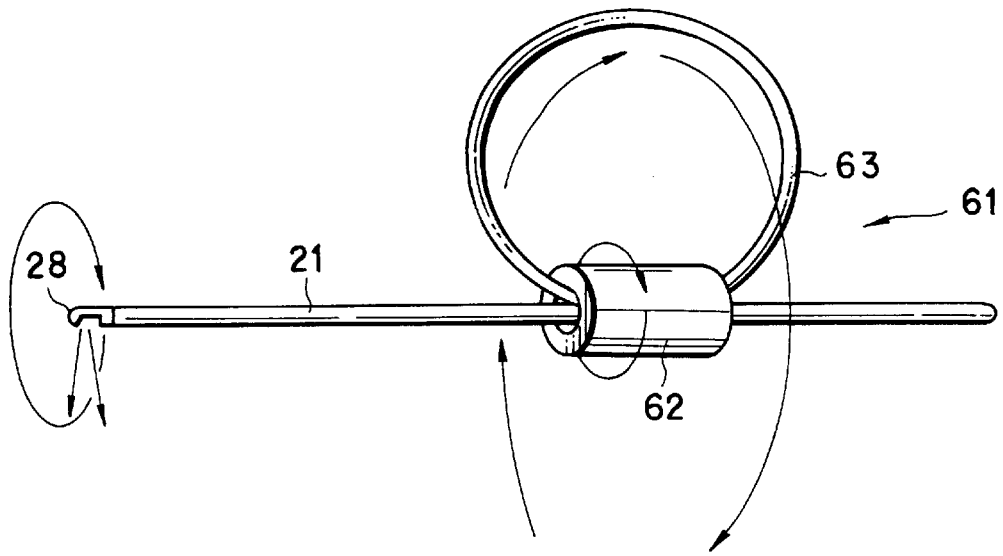
F I G. 12A
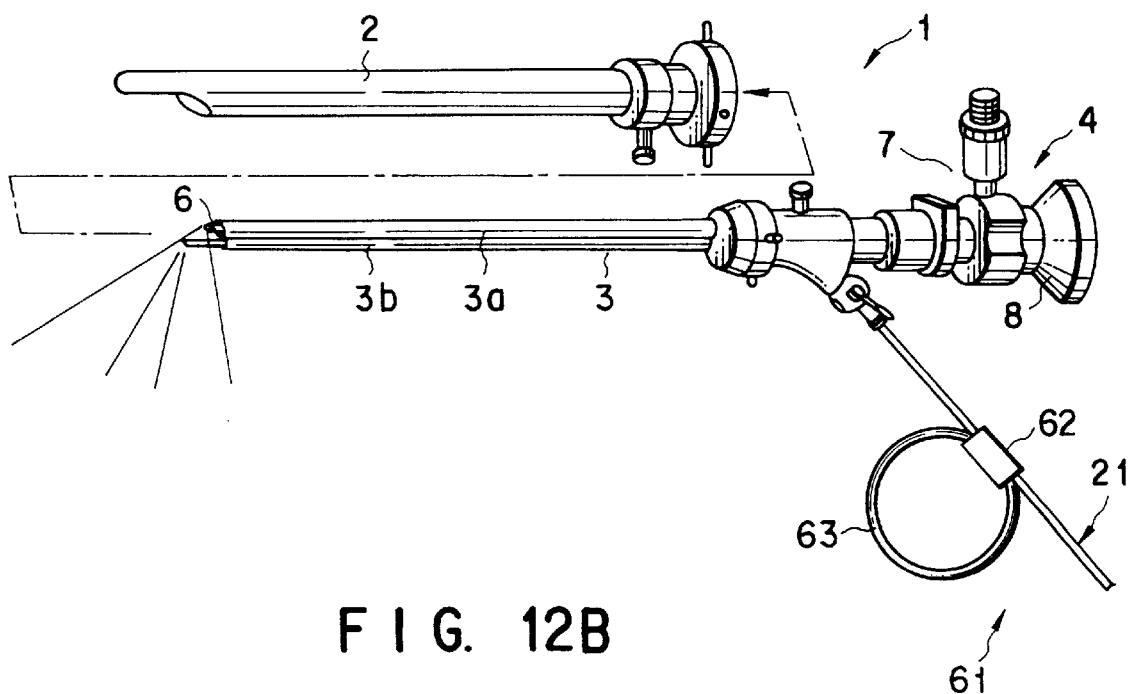
F I G. 12B

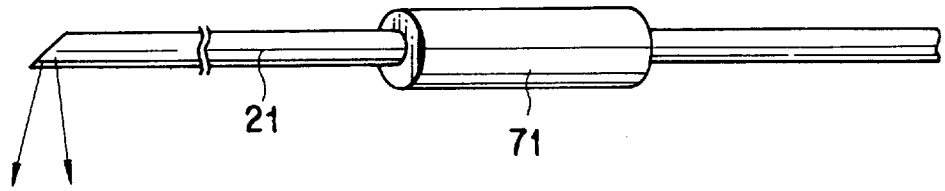
F I G. 13
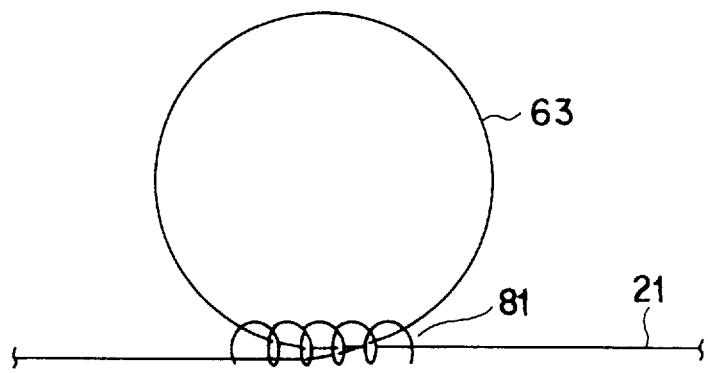
F I G. 14
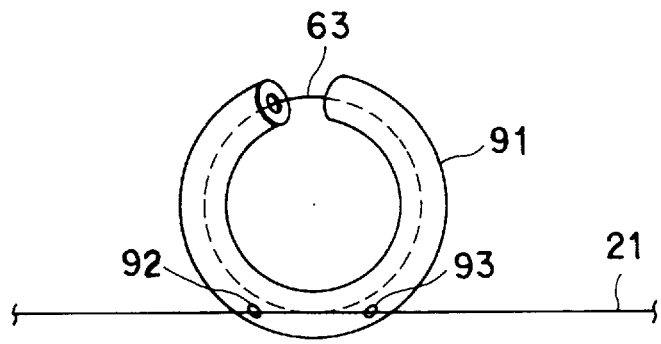
F I G. 15

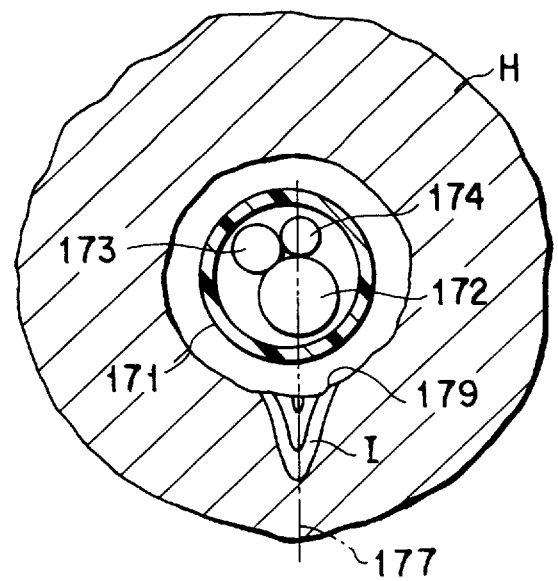
F I G. 23A
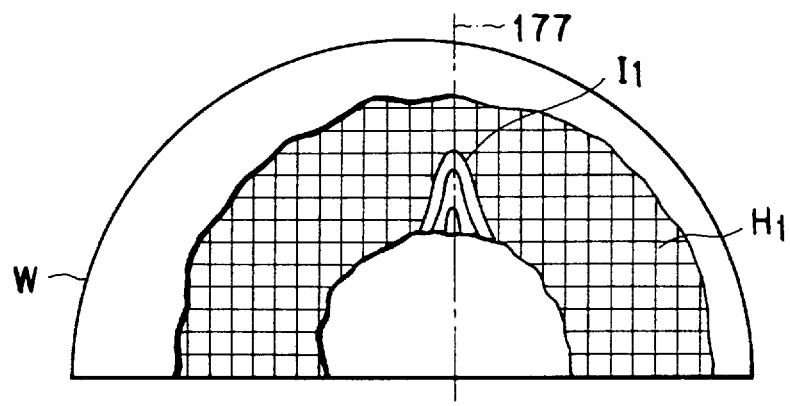
F I G. 23B
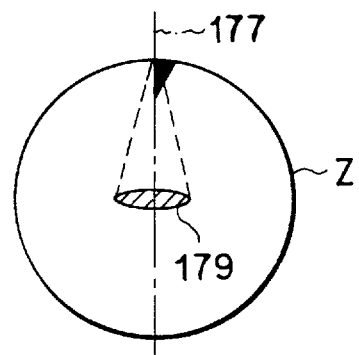
F I G. 23C

LASER PROBE

This application is a Continuation of application Ser. No. 08/297,803, filed Aug. 30, 1994.

BACKGROUND OF THE INVENTION

1. Field of the Invention

The present invention relates to a laser probe for use in a laser medical treatment apparatus for performing medical treatment by radiating a laser beam to a living tissue, e.g. a hypertrophied prostate tissue, on the inner wall of a tubular cavity internal organ, e.g., the prostate.

2. Description of the Related Art

In general, techniques of radiating a laser beam to a hypertrophied prostate tissue to transpire, coagulate and heat it have been developed, including methods of treating prostatomegaly (BPH: Benign Prostate Hyperplasia) under observation by means of an endoscope via the urethra.

The prostate is a tubular cavity internal organ and a hypertrophied tissue thereof forms on the inner wall of the tubular cavity organ. Thus, in the BPH treatment by means of radiation of a laser beam, the laser beam needs to be emitted in a lateral direction with respect to the axis of a laser beam guiding laser probe. The same applies to the treatment of a blood vessel.

For example, International Publication No. WO93/12728 discloses, as prior art, a technique wherein a metallic laser beam reflection member is provided at a distal end portion of a laser probe and a laser beam emitted from the laser probe is deflected laterally by the laser beam reflection member, thereby to apply the laser beam to a hypertrophied tissue located laterally with respect to the axis of the laser probe.

The reflection surface of the metallic reflection member used in the prior art of WO93/12728 is unable to reflect all received laser beam light. Consequently, part of the laser beam radiated on the reflection member is absorbed in the reflection member and converted to heat.

In order to prevent heating of the reflection member, a cooling fluid is supplied to the periphery of the reflection member via a fluid passage provided in an endoscope. However, the cooling fluid cannot directly be supplied to the reflection surface of the reflection member, which is heated to a high temperature. Thus, the reflection member cannot be cooled sufficiently.

There is a case where a tissue portion, blood, etc. dispersed by the radiated laser beam adhere to the reflection surface of the reflection member. In the prior art, such adhered matter cannot fully be removed. Consequently, the amount of laser beam light absorbed in the reflection surface of the reflection member increases and the temperature of the reflection surface may further rise. Moreover, because of the matter adhered to the reflection surface of the reflection member, the laser beam reflection efficiency of the reflection surface deteriorates and the reflection surface absorbs the laser beam more and more. As a result, the reflection member may be burnt and destroyed.

In this conventional laser probe the reflection member is integrated with a laser beam guiding optical fiber. Thus, when the reflection member is destroyed, the entire laser probe needs to be replaced, resulting in a high cost.

Another prior-art technique is disclosed in International Publication WO93/03678. In this document, like WO93/12728, a metallic laser beam reflection member is provided at a distal end portion of a laser probe. In WO93/03678, the reflection member is cooled by a liquid present around the distal end portion of the laser probe.

However, in WO93/03678, since both the reflection member and the liquid are heated by the radiated laser beam, the cooling effect of the reflection member deteriorates. In addition, the amount of cooling liquid supplied to the reflection surface of the reflection member cannot be controlled, and adhered matter such as a tissue portion, blood, etc. dispersed by the radiated laser beam cannot fully be removed.

Furthermore, the liquid present around the reflection member is not necessarily transparent or pure. Consequently, in this prior art, too, the reflection surface may be burnt and the reflection member destroyed.

Besides, in the laser probe of this prior art, an emission end portion of the optical fiber is fixed to the reflection member by clamping a leg portion (i.e. a clamping sleeve) of the reflection member. Accordingly, if the reflection member is destroyed, the entire laser probe needs to be replaced, resulting in a high cost. Moreover, the optical fiber on which the leg portion of the reflection member had been clamped deforms. If the reflection member of this conventional laser probe were to be detached, though not easily, from the optical fiber, the method of detachment would be complex. Thus, the replacement of the reflection member would be difficult and time-consuming.

SUMMARY OF THE INVENTION

The present invention has been made in consideration of the above circumstances, and the object thereof is to provide a laser probe with high cost performance which is capable of efficiently cooling a laser beam reflection tip to prevent damage to the laser beam reflection tip, which enhance the laser beam reflection tip very easily, and enhancing laser beam radiation efficiency.

In order to achieve the above object, there is provided a laser probe comprising an optical fiber for guiding a laser beam, a holder fixed at an end portion of the optical fiber, and a reflection tip detachably attached to the holder and having a reflection surface for reflecting the laser beam emitted from the optical fiber.

The laser beam reflection tip can be replaced very easily by detachably attaching the laser beam reflection tip to the holder of the laser beam guiding fiber.

The laser beam reflection tip is efficiently cooled to prevent damage to the laser beam reflection tip by flowing the cooling fluid through the vicinity of the laser beam guiding fiber and the laser beam reflection tip.

According to the present invention, therefore, the laser beam reflection tip can be efficiently cooled to prevent damage thereto, the laser beam reflection tip can be replaced very easily, and the laser beam radiation efficiency can be enhanced with high cost performance.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out in the appended claims.

BRIEF DESCRIPTION OF THE DRAWINGS

The accompanying drawings, which are incorporated in and constitute a part of the specification, illustrate presently preferred embodiments of the invention, and together with the general description given above and the detailed description of the preferred embodiments given below, serve to explain the principles of the invention.

FIG. 4 is a perspective view showing schematically the structure of a urethroscope in which the laser probe of the first embodiment is built;

FIG. 5 is a side view showing a discharge port at a distal end portion of an outer sheath of the urethroscope;

FIG. 6 is a vertical cross-sectional view showing a main portion of a second embodiment of the invention;

FIG. 7A is a vertical cross-sectional view showing a main portion of a third embodiment of the invention;

FIG. 7B is a vertical cross-sectional view showing a main portion of a fourth embodiment of the invention;

FIG. 7C is a vertical cross-sectional view showing a main portion of a fifth embodiment of the invention;

FIG. 7D is a vertical cross-sectional view showing a main portion of a sixth embodiment of the invention;

FIG. 8 is a vertical cross-sectional view showing a main portion of a seventh embodiment of the invention;

FIG. 12A is a perspective view showing a rotational adjustment unit of the laser probe;

FIG. 12B is a perspective view showing the state in which the laser probe shown in FIG. 12A is used in combination with an endoscope;

FIG. 13 is a perspective view showing a grip of the laser probe;

FIG. 14 is a perspective view showing a first modification of the rotational adjustment unit of the laser probe;

FIG. 15 is a perspective view showing a second modification of the rotational adjustment unit of the laser probe;

FIG. 23A is a cross-sectional view taken along line $23A_1$–$23A_2$–$23A_3$–$23A_4$ in FIG. 22;

FIG. 23B is a plan view of a diagnostic image in the depth direction of an affected part taken by an ultrasonic probe;

FIG. 23C is a plan view showing an observed image of the surface of the affected part taken by an optical scope tube;

DETAILED DESCRIPTION OF THE PREFERRED EMBODIMENTS

Figure 1:
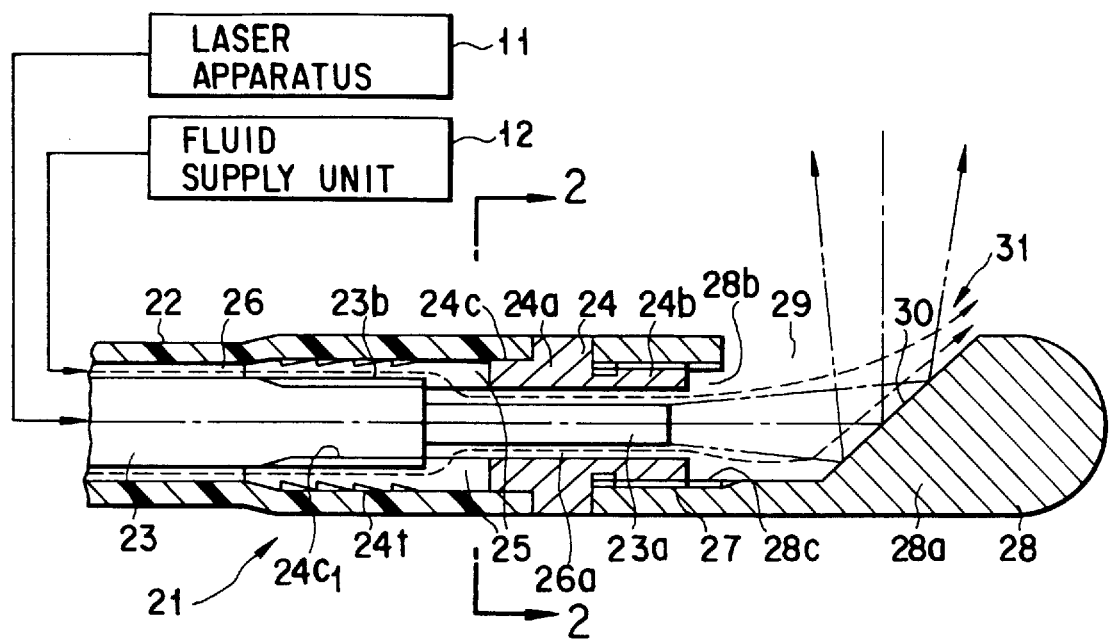
FIG. 1 is a vertical cross-sectional view showing schematically the structure of a main portion of a laser probe according to a first embodiment of the present invention.

A first embodiment of the present invention will now be described with reference to FIGS. 1 to 5. FIG. 1 shows schematically the structure of a lateral radiation type laser probe 21 having an outside diameter of 3 mm or less. The laser probe 21 comprises an outer tube 22 and an optical fiber 23, inserted in the outer tube 22, for guiding a laser beam. The optical fiber 23 has a beam incidence end portion and a beam emission end portion. The beam incidence end portion of the fiber 23 is connected to a laser apparatus 11 for generating a laser beam.

A substantially ring-shaped holder 24 is fixed at the beam emission end portion of the fiber 23. The outer peripheral surface of a holder body 24a of the holder 24 is provided with a distal end-side (beam emission side) small-diameter portion 24b and a rear end-side small-diameter portion 24c.

A distal end portion of the outer tube 22 is tightly fitted on the rear end-side small-diameter portion 24c of the holder body 24a. The outer peripheral surface of the rear end-side small-diameter portion 24c is provided with a sawtooth-like irregular portion 24t for preventing removal. When the distal end portion of the outer tube 22 is tightly fitted on the rear end-side small-diameter portion 24c of the holder body 24a, projections of the irregular portion 24t of the small-diameter portion 24c bite the inner peripheral surface of the tube 22. Thereby, the outer tube 22 is prevented from being removed from the small-diameter portion 24c of the holder body 24a.

The inner peripheral surface of the rear end-side small-diameter portion 24c of the holder 24 is provided with an irregular portion (screw hole portion) $24c_1$ such as thread ridges. The irregular portion $24c_1$ constitutes an engaging portion with the emission side end portion of the optical fiber 23.

The optical fiber 23 comprises a core 23a situated at the axis of the fiber 23 and a jacket (or outer sheath) 23b provided around the core 23a. The inside diameter of the holder body 24a is greater than the outside diameter of the core 23a of the fiber 23. The beam emission-side end portion of the optical fiber 23 includes an exposed core 23a from which the jacket 23b is removed. As is shown in FIG. 1, on the beam emission side of the fiber 23, a gap 26a is provided between the exposed core 23a of the fiber 23 and the inner peripheral surface of the holder body 24a. The outer peripheral surface of the jacket 23b of the fiber 23 bites into the irregular portion 24c 1 of the holder body 24a, and thereby the holder body 24a and the optical fiber 23 are firmly engaged.

A fluid passage 26 is formed between the outer tube 22 and the optical fiber 23. A proximal end portion of the fluid passage 26 is connected to a fluid supply unit (cooling fluid supply means) 12 in which a supply pump (not shown), etc. are housed. When a laser beam is radiated from the laser probe 21, the fluid supply unit 12 is driven to supply a cooling fluid to the fluid passage 26. In this case, the cooling fluid used is a liquid affinitive to the living body, since it is absorbed in the body.

Figure 2:
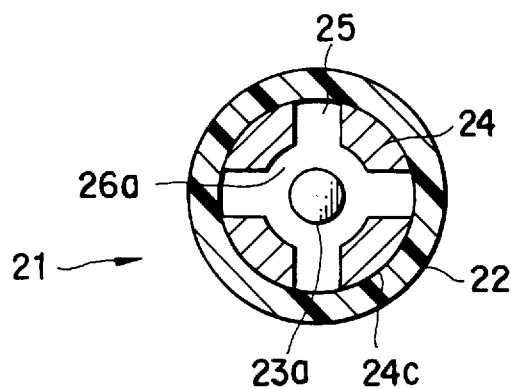
FIG. 2 is a cross-sectional view taken along line 2—2 in FIG. 1.

As is shown in FIG. 2, the rear end-side small-diameter portion 24c of the holder 24 is provided with a plurality of slits 25 at contact parts with the outer tube 22. A distal end portion of the fluid passage 26 between the tube 22 and fiber 23 communicates with a space (a gap 26a between the exposed core 23a of fiber 23 and the inner peripheral surface of the holder body 24a) in front of the engaged part between the small-diameter portion 24c and the jacket 23b of the fiber 23 via the slits 25 of the holder 24.

The outer peripheral surface of the distal end-side small-diameter portion 24b of the holder 24 is provided with a male screw portion 27. A reflection tip 28 formed of a metallic material such as a stainless steel is detachably attached to the male screw portion 27 of the small-diameter portion 24b. A laser beam input port 28b is formed in a body 28a of the reflection tip 28 on the proximal end side of the body 28a. The inner peripheral surface of the laser beam input port 28b is provided with a female screw portion 28c which is to be meshed with the male screw portion 27 of the distal end-side small-diameter portion 24b. The reflection tip body 28a is detachably coupled to the distal end portion of the holder 24 by means of engagement between, the female screw portion 28c and the male screw portion 27 of the holder 24.

The outer peripheral surface of the reflection tip body 28a is provided with a laser beam output port 29 communicating with the laser beam input port 28b. An inner bottom part of the beam input port 28b of the reflection tip body 28a, which bottom part faces the laser beam emission end of the fiber 23, is provided with a laser beam reflection surface 30 inclined, e.g. at about 45° with respect to the optical axis of the laser beam emitted from the optical fiber 23. The reflection surface 30 may be inclined at 30° to 70° with respect to the optical axis of the laser beam emitted from the optical fiber 23.

The reflection surface 30 is processed to have a mirror surface for reflecting a laser beam, for example, by means of buffing or chemical polishing.

When a laser beam is radiated, the laser beam emitted from the emission end of the core 23a of optical fiber 23 is reflected by the reflection surface 30 towards the laser beam output port 29, as shown by arrows in FIG. 1. The reflected beam is radiated in a lateral direction of the laser probe 21 through the beam output port 29.

The reflection surface 30 of the reflection tip 28a may be plated with gold, platinum, etc., when it is processed, thereby to enhance the reflectance. Furthermore, the processed reflection surface 30 may be plated after it is subjected to buffing or chemical polishing.

If the processed reflection surface 30 is plated after it is subjected to buffing or chemical polishing, the basic layer of the reflection surface 30 is smoother than that of the surface 30 plated after simple processing. Thus, a good reflection surface is obtained only by forming a thin plating layer having a thickness of, e.g. about 10 $\mu$m or less. Accordingly, the reflection efficiency of the laser beam can be enhanced.

Moreover, as compared to the case where reflection surface 30 is coated with gold without the polishing process or reflection tip body 30 is formed of gold itself, a simpler, lower-cost, and higher-performance reflection surface 30 can be obtained in the present embodiment. The reflection surface 30 of this embodiment, which is plated after buffing, has a high reflectance of 90% or higher.

The fluid passage 26 between the outer tube 22 and optical fiber 23 communicates with the laser beam input port 28b of the reflection tip body 28a via the slits 25 of the holder 24 and the gap 26a between the holder body 24a and the core 23a of the optical fiber 23 successively. Thereby, cooling fluid flowing means 31 for flowing a cooling fluid to the surroundings of the optical fiber 23 and reflection tip 28 is constituted.

Since the laser probe 21 of the present embodiment is used in the state in which it is inserted in an endoscope such as an urethroscope 1, it is desirable that the outside diameter of the laser probe 21 be set at about 3 mm or less. In the present embodiment, the outside diameter of the reflection tip 28 of the laser probe 21 is set at 2.3 mm, and the outside diameter of the outer tube 22 is made substantially equal to that of the reflection tip 28.

The operation of the laser probe having the structure will now be described. When a laser beam is radiated from the laser probe 21, the laser beam emitted from the optical fiber 23 of the laser probe 21 is reflected by the reflection surface 30 of the reflection tip body 28a. The reflected beam is emitted in a lateral direction of the laser probe 21. When the laser beam is radiated, most of the beam is reflected by the reflection surface 30 of the reflection tip body 28a and applied to a living tissue, e.g. a hypertrophied prostate tissue, on the inner wall of a tubular cavity internal organ, e.g. the prostate.

In addition, when the laser beam is radiated from the laser probe 21, a cooling fluid is supplied to the fluid passage 26 defined between the optical fiber 23 and the outer tube 22. As is indicated by broken-line arrows in FIG. 1, the cooling fluid is made to flow from the fluid passage defined between the optical fiber 23 and outer tube 22 to the laser beam input port 28b of the reflection tip body 28a via the slits 25 of the holder 24 and the gap 26a between the holder body 24a and the core 23a of the optical fiber 23 successively. Thereafter, the cooling fluid is let to flow to the outside of the laser probe 21 from the laser beam output port 29.

The laser probe having the above structure has the following advantages. When the laser beam is radiated from the laser probe 21, the cooling fluid is supplied by the cooling fluid flowing means 31 to the surroundings of the optical fiber 23 and reflection tip 28. The optical fiber 23 and reflection tip 28 can be effectively cooled by the flow of the cooling fluid. Thus, the following undesirable situation is prevented from occurring: part of the emitted laser beam is absorbed in the reflection tip body 28a so that the reflection tip body 28a is heated to a high temperature. Accordingly, destruction of the reflection tip 28 can be prevented.

Even if the reflection tip 28 is heated by the radiated laser beam and air bubbles adhere to the reflection surface 30 of the reflection tip body 28a and the surroundings thereof, such air bubbles adhering to the reflection surface 30 of the reflection tip body 28a and the surroundings thereof can be removed by the flow of the cooling fluid within the laser probe 21. Thus, the following undesirable situation is prevented from occurring: normal reflection of the laser beam is prevented by the air bubbles adhering to the reflection surface 30 of the reflection tip body 28a and the surroundings thereof. Accordingly, the laser beam can be radiated stably at all times.

In addition, the flow of the cooling fluid within the laser probe 21 can prevent tissue portions dispersed by the radiated laser beam, blood due to hemorrhage, etc. from adhering to the reflection surface 30. Thus, the reflection surface 30 of the reflection tip body 28a is not contaminated. Thus, a so-called "burning phenomenon" of the reflection surface 30 can be prevented, in which the reflectance of the reflection surface 30 is decreased owing to the burning of the reflection surface 30 due to the contamination of the reflection surface 30 of the reflection tip body 28a.

Figure 3A:
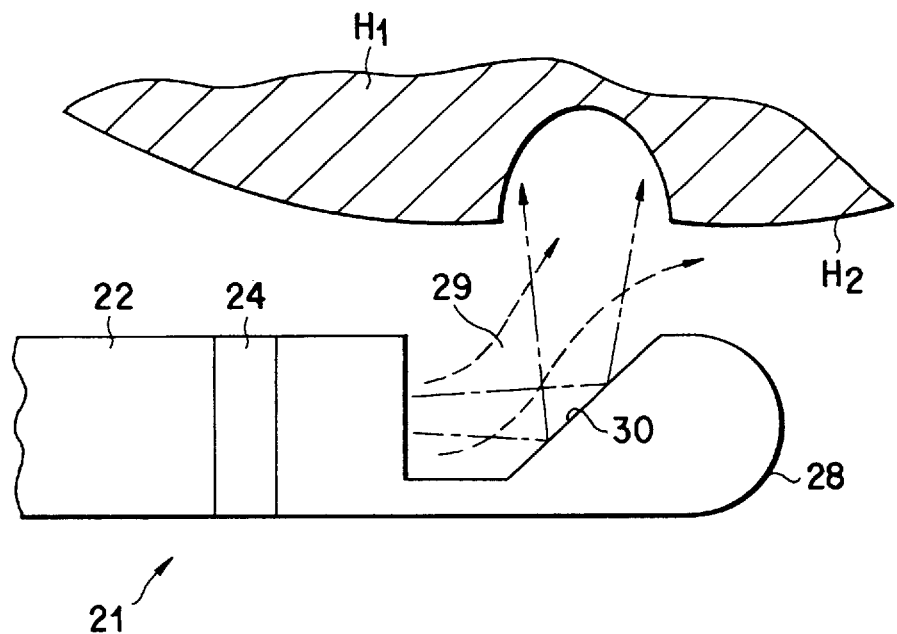
FIG. 3A is a side view showing the state of medical treatment for a prostate tissue by the laser probe of the first embodiment.

As is shown in FIG. 3A, the flow of the cooling fluid discharged to the outside of the laser probe 21 from the laser beam output port 29 of the laser probe 21 can remove air bubbles, tissue portions, blood, etc. existing on the laser beam path between the prostate tissue $H_1$ and the reflection tip body 28a. Thereby, the optical path of the laser beam emitted from the laser probe 21 can be kept clean at all times, and the laser beam emitted from the laser probe 21 can be efficiently guided to the prostate tissue $H_1$.

Furthermore, the cooling fluid discharged to the outside of the laser probe 21 from the laser beam output port 29 of the laser probe 21 can cool not only the reflection tip body 28a but also a urethral surface (urethral mucosa) $H_2$ of the prostate portion of the prostate tissue $H_1$. Thereby, while the urethral mucosa $H_2$ is hardly cauterized (or heated), the intra-prostate tissue (called internal gland) $H_1$ which causes prostatomegaly can be effectively cauterized (or heated).

Since the reflection surface 30 of the reflection tip body 28a can be efficiently cooled by the flow of the cooling fluid within the laser probe 21, the amount of the supplied cooling fluid can be reduced. Thereby, the following undesirable situation can be avoided from occurring: for example, in the case where the reflection tip 28 is cooled by water supplied from the urethroscope 1, the cooling fluid flows over the outer surface of the reflection tip 28 and the cooling fluid is not directly supplied to the laser beam reflection surface 30, as a result of which a great amount of water is needed to compensate the lowering of the cooling efficiency of the reflection tip 28. Thus, a great amount of cooling fluid is absorbed in the living body, and the balance among body fluid components is maintained.

Figure 3B:
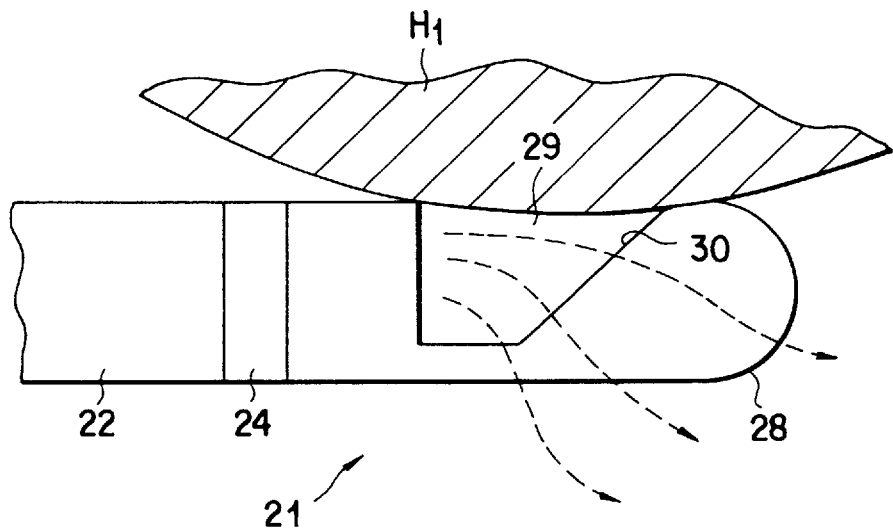
FIG. 3B is a side view showing the state in which a laser beam output port of the laser probe of the first embodiment is closed by the prostate tissue.

FIG. 3B illustrates the case where a distance is not provided between the prostate tissue $H_1$ and the laser beam output port 29 of reflection tip 28 of laser probe 21 according to the present invention, so that the laser beam output port 29 is closed by the prostate tissue $H_1$. In this case, the cooling fluid within the laser probe 21 can be discharged to the outside of the laser probe 21 from the side opening of the reflection tip body 28a. Thus, even if the reflection tip 28 is put in close contact with the prostate tissue $H_1$, a sufficient amount of cooling fluid can be supplied without degrading the cooling efficiency of the reflection surface 30 of the reflection tip body 28a.

The reflection tip 28 is detachably attached to the front-side small-diameter portion 24b of the holder 24. Thus, even if the reflection surface 30 of the reflection tip 28 is burnt, the reflection tip 28 alone can be replaced very easily. As compared to the case where the entire laser probe 21 is replaced, the maintenance cost is reduced.

In the laser probe 21 of the present embodiment, the outside diameter of the outer tube 22 is substantially equal to that of the reflection tip 28. Thus, the outer tube 22 and the reflection tip 28 are easily aligned with little loosening. In the case of the prior-art laser probe wherein only the tip portion is thick and the fiber is thin, when the laser probe is inserted into the endoscope in use, the laser probe is loosened in the state in which the tip is projected from the end of the endoscope and the alignment becomes difficult. This problem is solved by the present embodiment.

FIG. 4 shows schematically the structure of an endoscope, e.g. urethroscope 1, in which the laser probe 21 of the present embodiment is built. In FIG. 4, reference numeral 2 denotes an outer sheath of the urethroscope 1 and numeral 3 denotes an inner sheath inserted in the outer sheath 2.

The inner sheath 3 is provided with an optical scope tube insertion portion 3a in which an optical scope tube 4 is inserted, and a forceps insertion portion 3b, provided substantially in parallel to the optical scope tube 4, for insertion of the laser probe 21.

The optical scope tube 4 includes an insertion portion 6 inserted into the living body, and a proximal structure 7 connected to a proximal end portion of the insertion portion 6. The proximal structure 7 is provided with an eyepiece 8 in which an eyepiece lens is built. The insertion portion 6 of the optical scope tube 4 is inserted in the optical scope tube insertion portion 3a of the inner sheath 3.

A fluid supply passage is provided within the inner sheath 3. A fluid discharge passage is provided between the inner sheath 3 and outer sheath 2. A fluid discharged from a distal opening portion of the inner sheath 3 is let to flow to the fluid discharge passage provided between the inner sheath 3 and outer sheath 2. Thus, the fluid is supplied and discharged from the urethroscope 1. This type of endoscope is generally called "continuous perfusion type" endoscope. A plurality of discharge ports 32 are formed at a distal end portion of the outer sheath, as shown in FIG. 5.

At the time of laser medical treatment using the urethroscope 1, the optical scope tube 4 and laser probe 21 are inserted in the inner sheath 3 of the urethroscope 1. With the inner sheath 3 covered with the outer sheath 2, the insertion portion of the urethroscope 1 is inserted into the living body via the urethroscope. In this case, as shown in FIG. 4, the distal end portion of the laser probe 21 extends in front of an observation portion of the optical scope tube 4, and the laser radiation is effected in the state in which an area of laser beam radiation by the laser probe 21 is present within a visual field of the optical scope tube 4.

When the laser probe 21 of this embodiment is used under the observation by the continuous perfusion type urethroscope 1, a highly transparent, pure liquid supplied from the inner sheath 3 of the urethroscope 1 is used to keep the visual field of the optical scope tube 4 of urethroscope 1 and to cool the distal end portion of the laser probe 21. If the pressure within the bladder reaches a predetermined level, the liquid supplied to the bladder is introduced into the fluid discharge passage defined between the outer sheath 2 and inner sheath 3 via the discharge ports 32 of the outer sheath 2, and the liquid is discharged to the outside through the liquid discharge passage.

In this case, not only the pure liquid supplied from the inner sheath 3 of the urethroscope 1 but also a contaminated liquid with low transparence is present around the reflection tip 28 at the end of the laser probe 21.

According to the laser probe 21 of the present embodiment, the pure cooling liquid within the laser probe 21 is supplied to the reflection surface 30 of the reflection tip 28, and the contaminated liquid can be surely removed from the surroundings of the reflection surface 30. Thus, when the laser probe 21 is used under the observation by the continuous perfusion type urethroscope 1, even if a contaminated liquid with low transparence is present around the reflection tip 28, the contaminated liquid can be surely removed from the surroundings of the reflection surface 30 by the flow of the cooling liquid within the laser probe 21. Therefore, the present embodiment is effective in preventing burning of the reflection surface 30.

If burning of the reflection surface 30 has occurred, the reflection tip body 28a is rotated in a direction opposite to the direction for engagement. Thereby, the reflection tip body 28a is removed from the holder 24 and the reflection tip body 28a alone can be replaced very easily with a new reflection tip body 28a. As compared to the case where the entire laser probe 21 is replaced, the maintenance cost is very low.

FIG. 6 shows a second embodiment of the invention. In the second embodiment, the relationship in the first embodiment between the screw portion of the holder 24 of the laser probe 21 and the screw portion of the reflection tip body 28a is reversed. Specifically, in the second embodiment, the reflection tip body 28a is provided with a male screw portion 33, and the holder 24 is provided with a female screw portion 34 meshed with the male screw portion 33.

FIGS. 7A to 10 show other embodiments wherein the reflection surface 30 of the reflection tip body 28a of the laser beam lateral emission type laser probe 21 according to the first embodiment is modified to change the shape of the laser beam emitted in the lateral direction.

In the embodiments shown in FIGS. 7A to 7D, the reflection surface 30 of the reflection tip body 28a is formed in a spherical shape. In this case, the "spherical shape" does not necessary mean the "real" spherical shape but it means any spherical shape capable of changing the widening (divergence) angle of the laser beam independently in two mutually perpendicular axial directions on a wave front of the laterally emitted laser beam (i.e. a plane perpendicular to the laser beam emission direction).

In the embodiments of FIGS. 7A to 7D, the widening angle of the laterally emitted beam is changed in the axial direction of the laser probe 21 and a direction perpendicular to this axial direction. The axial direction of the laser probe 21 is substantially parallel to the axial direction of the urethra of the prostate part. Accordingly, in the embodiments of FIGS. 7A to 7D, the widening angle of the laterally emitted beam can be changed in the axial direction of the urethra of the prostate part and the direction perpendicular to this axial direction.

In the laser probe 21 of the third embodiment as shown in FIG. 7A, the reflection tip body 28a is provided with a convex reflection surface 30A. As compared to the first embodiment wherein the laser probe 21 is provided with flat reflection surface 30, the widening angle of the laterally emitted laser beam can be increased both in the axial direction of the urethra of the prostate and the direction perpendicular to this axial direction. The radius of the spherical reflection surface 30A is set at about 1 mm to 3 mm.

With the laser probe 21 having the reflection surface 30A of the reflection tip body 28a according to the third embodiment, a laser beam with low energy density can be applied to a wide area of the tissue of the living body. According to the third embodiment, if the prostatomegaly is not relatively serious (i.e. the degree of hypertrophy of the prostate is low) and a relatively low cautery effect on the prostate tissue is adequate, the time needed for the surgical operation can be shortened by the wide-range laser radiation.

In the laser probe 21 according to the fourth embodiment as shown in FIG. 7B, the reflection tip body 28a is provided with a concave reflection surface 30B. As compared to the first embodiment wherein the laser probe 21 is provided with flat reflection surface 30, the widening angle of the laterally emitted laser beam can be decreased both in the axial direction of the urethra of the prostate and the direction perpendicular to this axial direction. The radius of the spherical reflection surface 30B is set at about 1 mm to 3 mm.

With the laser probe 21 having the reflection surface 30B of the reflection tip body 28a according to the fourth embodiment, a laser beam with high energy density can be applied to a narrow area of the tissue of the living body. The fourth embodiment is effective if the prostatomegaly is relatively serious (i.e. the degree of hypertrophy of the prostate is high) and a laser beam with high energy density and high cautery effect needs to be applied to the prostate tissue.

In the laser probe 21 according to the fifth embodiment as shown in FIG. 7C, the reflection tip body 28a is provided with a concave reflection surface 30C having less of a radius of curvature than the reflection surface 30B shown in FIG. 7B. In this case, a laser beam emitted laterally from the laser probe 21 is once focused and then diverged.

With the above structure, a focal point f of the reflection surface 30C is present outside the laser beam output port 29 of the reflection tip body 28a. Thus, if the laser beam is emitted with the distance between the reflection tip 28 and the body tissue being kept short, the laser beam can be focused within the body tissue. Moreover, since the energy density is very high at the focal point f of the reflection surface 30C, the fifth embodiment is very effective if a very high tissue cautery effect is required in a narrow area, e.g. in the case of calculi lithotrity.

In the laser probe 21 according to the sixth embodiment as shown in FIG. 7D, the reflection tip body 28a is provided with a concave reflection surface 30D having a focal point f within the laser beam output port 29 of the reflection tip 28. In this case, a laser beam with low energy density can be applied to the body tissue. The shape of the beam emitted from the reflection surface 30D is substantially equal to that of the beam emitted from the convex reflection surface 30A as shown in FIG. 7A.

With the above structure, since the reflection tip 28 is provided with the concave reflection surface 30D, the processing of the reflection surface 30D is easier than in the case where the convex reflection surface 30A is formed on the tip 28. Moreover, the cooling fluid can be surely supplied to the entire reflection surface 30D.

Furthermore, if the focal point of the laser beam is present inside the laser beam output port 29, as with the case of the concave reflection surface 30D of the reflection tip 28 of the 6th embodiment, the laser beam is not focused within the body tissue. Even if the focusing of the beam is erroneously effected, no excessive cautery effect is exerted on the living body tissue and the laser beam can be applied safely.

Figure 9:
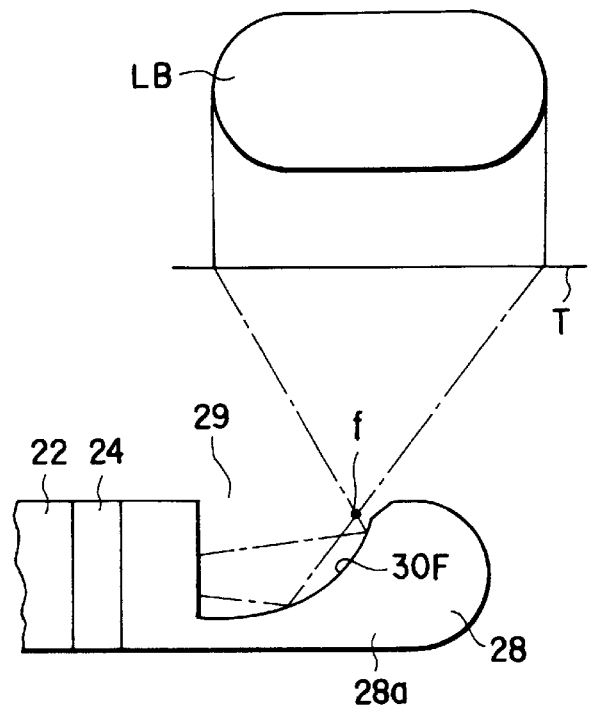
FIG. 9 is a vertical cross-sectional view showing a main portion of an eighth embodiment of the invention.

FIGS. 8 and 9 show other embodiments wherein the reflection tip 28a of the lateral emission type laser probe 21 according to the first embodiment is provided with a curved (not spherical) reflection surface 30. In the case of the spherical reflection surface 30 of the reflection tip body 28a the widening angle of the laser beam is changed into directions (i.e. two axial directions perpendicular to each other in a plane perpendicular to the laser beam emission direction), whereas in the case of the curved reflection surface 30, the widening angle of the beam is changed only in one direction.

In the laser probe 21 of the seventh embodiment as shown in FIG. 8, the reflection tip body 28a is provided with a convex reflection surface 30E. In the laser probe 21 of the eighth embodiment as shown in FIG. 9, the reflection tip body 28a is provided with a concave reflection surface 30F.

The radius of each of the reflection surfaces 30E and 30F is set about 1 mm to 3 mm.

In the case of the convex reflection surface 30E shown in FIG. 8 and the concave reflection surface 30F shown in FIG. 9, the widening angle of the laser beam is changed in the axial direction of the laser probe 21. In addition, in the case of the reflection tip body 28a of the laser probe 21 of each of the seventh and eighth embodiments, the laser beam emitted from the laser probe 21 is diverged in the axial direction of the laser probe 21.

Thus, the longitudinal axis of the laser beam emitted from the laser probe 21 of each of the seventh and eighth embodiments is parallel to the axial direction of the urethra of the prostate part. Therefore, this shape of the laser beam is very advantageous in cauterizing the prostate. Specifically, when the laser beam is emitted within the urethra of the prostate from the laser probe 21 of the seventh or eighth embodiment, the laser beam can be prevented from being applied to, e.g. a thin prostate tissue located in a direction perpendicular to the axis of the urethra of the prostate (e.g. 6-o'clock or 12-o'clock direction). Thus, there is no concern that the laser beam is excessively radiated onto the thin prostate tissue, and no hole is made in the prostate tissue by the laser beam radiation.

In the seventh and eighth embodiments, the laser beam having an oval cross section with a longitudinal axis parallel to the axis of the urethra of the prostate is emitted from the laser probe 21. Thereby, the widening angle of the laser beam in the direction perpendicular to the axis of the urethra of the prostate can be decreased. Thus, the laser beam is prevented from being applied in the 6-o'clock or 12-o'clock direction perpendicular to the axis of the urethra of the prostate. By contrast, in the case of the reflection surfaces 30A and 30C as shown in FIGS. 7A and 7C, the laser beam with a substantially oval cross section extending in both the axial direction of the urethra of the prostate and the direction perpendicular to this axial direction is also emitted in the 6-o'clock or 12-o'clock direction perpendicular to the axis of the urethra of the prostate. This can be prevented in the seventh and eighth embodiments. When an area located in a direction perpendicular to the axis of the urethra of the prostate, e.g. seminal colliculus located in the 6-o'clock, is cauterized, the side effect of the operation, e.g. retrograde emission, can be prevented.

Normally, in the case of prostatomegaly, the tissue extends considerably in the axial direction of the urethra of the prostate (e.g. about 3 cm to 5 cm in the length of the urethra of the prostate). Accordingly, if the laser beam emitted from the laser probe 21 of each of the seventh and eighth embodiments, which beam has a cross section elongated in parallel to the axial direction of the urethra of the prostate, is applied to the affected part of the prostatomegaly, the laser beam can be efficiently radiated on the wide area of the tissue elongated along the axis of the urethra of the prostate. Therefore, the time-consuming operation in the case of the reflection tip 28 of FIG. 1 is not needed: if the laser beam with a small widening angle, which is emitted from the reflection tip 28 of FIG. 1, is applied to the affected tissue of prostatomegaly elongated along the axis of the urethra of the prostate, the reflection tip 28 needs to be moved along the axis of the urethra of the prostate and the laser beam radiation needs to be repeated many times. It will be appreciated that the laser beam that is reflected with have different magnification ratios in accordance with the different reflection directions. Therefore, according to the seventh and eighth embodiments, the efficiency of the laser medical treatment on the affected tissue of prostatomegaly can be enhanced, and the time for laser medical treatment can be decreased.

The area of the beam obtained by the reflection tip 28 of the convex reflection surface 30E shown in FIG. 8 or the concave reflection surface 30F shown in FIG. 9, which beam is elongated only in the axial direction of the laser probe 21, is less than that of the substantially circular beam obtained by the reflection surface 30A or 30C of the reflection tip 28 of FIG. 7A or FIG. 7C, if the maximum diameters of both beams are equal. Thus, the former beam has a greater energy density and a higher laser beam radiation effect. For example, when the outside diameter of the reflection tip body 28a shown in FIG. 9 is set at 2.3 mm and the radius of the reflection surface 30F of the reflection tip body 28a is set at 2.4 mm, the laser beam emitted from the optical fiber 23 having core 23a with a diameter of 600 μm at a divergence angle of about 15° is reflected by the reflection surface 30F, as shown in FIG. 9. The reflected beam is once converged at focal point f and then diverged at an angle of about 70° in the axial direction of the laser probe 21. The diverged beam is radiated on a distant radiation surface T as an elongated beam LB.

Figure 10:
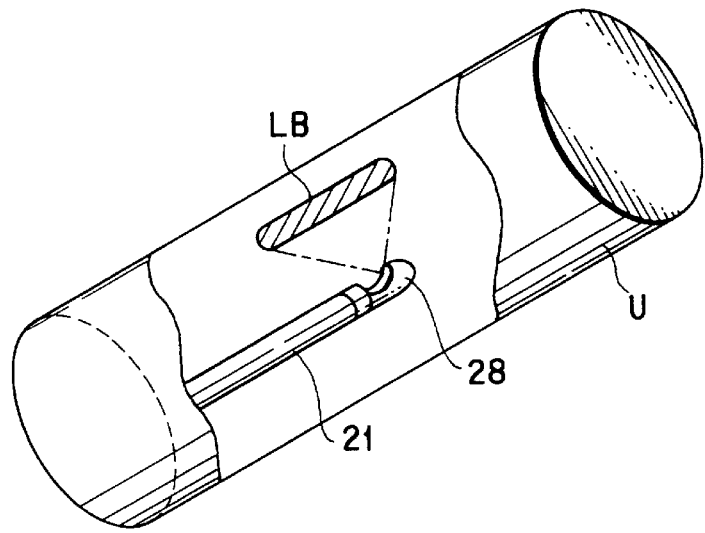
FIG. 10 is a perspective view of a main portion of the laser probe of the eighth embodiment in the use state.

FIG. 10 shows a model wherein the laser probe 21 according to the eighth embodiment is used in the body tube or cavity such as the urethra U of the prostate. A laser beam LB emitted from the reflection tip 28 of the laser probe 21 has a substantially oval or rectangular shape elongated in the axial direction of the urethra U of the prostate.

The reflection tip body 28a of the laser probe 21 is provided with the convex reflection surface 30E as in the seventh embodiment or the concave reflection surface 30F as in the eighth embodiment and the laser beam emitted from the laser probe 21 has a substantially oval cross section elongated in the axial direction of the urethra U of the prostate. Thus, laser beam radiation can be effected in a wide area with high efficiency along the axis of the urethra U of the prostate, and the widening angle of the laser beam is narrowed along the axis perpendicular to the axis of the urethra U of the prostate. Thereby, cautery in the 6-o'clock direction or 12-o'clock direction can be prevented and the laser beam can be performed safely.

Like the embodiments as shown in FIGS. 7C and 7D, the radius of curvature of the concave reflection surface 30F of the reflection tip 28 as shown in FIG. 9 may be changed, so that the focal point f of the laser beam may be selectively located within or outside the laser beam output port 29 of the reflection tip 28.

Moreover, a laser beam of a desired shape can be obtained by freely choosing the shape of the reflection surface 30 of the reflection tip body 28a of the laser beam lateral emission type laser probe 21 of the first embodiment. In this case, an optimal laser beam shape can be chosen in accordance with the state of the prostate.

Figures 11A, 11B:
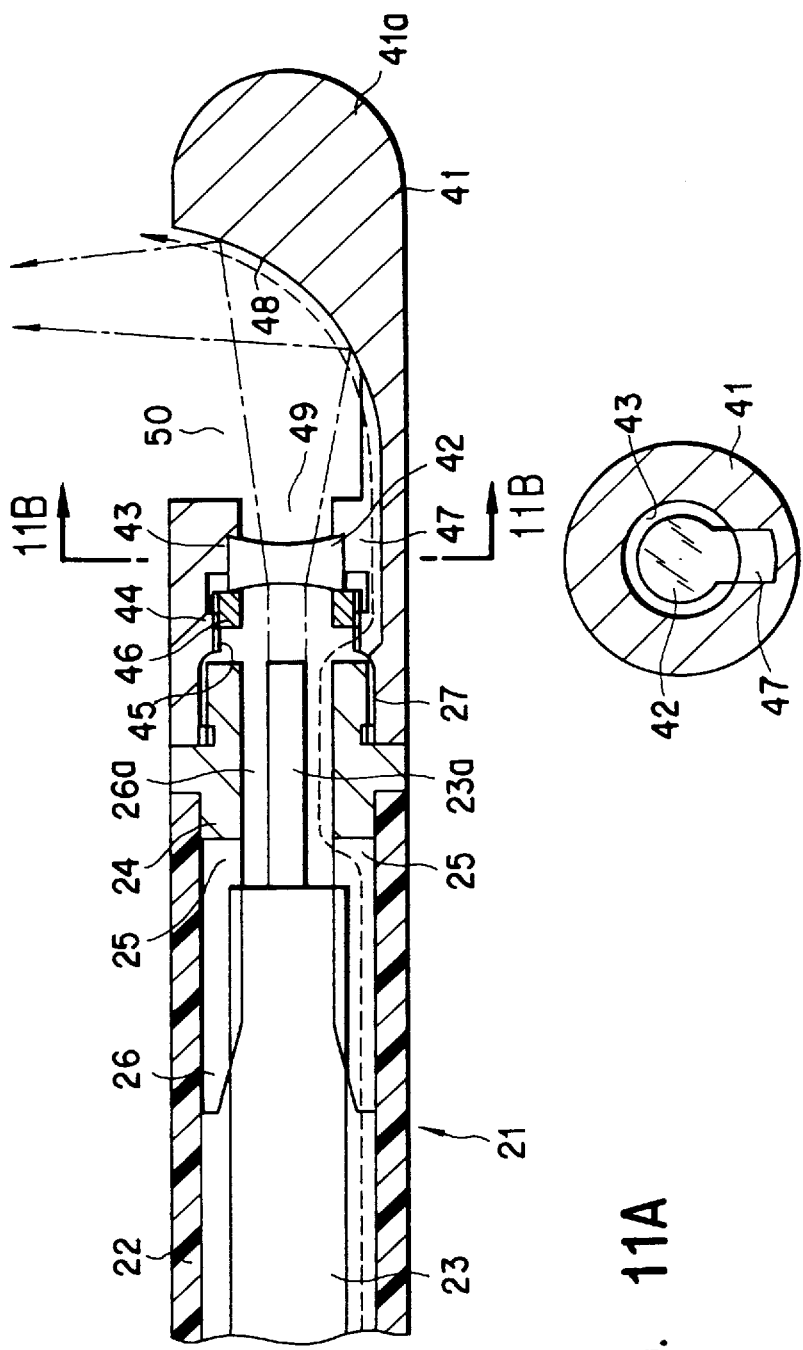
FIG. 11A is a vertical cross-sectional view showing a main portion of a laser probe of a ninth embodiment of the invention.
FIG. 11B is a cross-sectional view taken along line 11B—11B in FIG. 11A.

FIGS. 11A and 11B show a ninth embodiment of the present invention, wherein a part of the reflection tip 28 of the laser probe 21 of the first embodiment is modified. The structural elements common to those in the first embodiment are denoted by like reference numerals and a description thereof is omitted.

Specifically, a reflection tip body 41a of a reflection tip 41 is provided with a lens 42 which is situated in front of the core 23a of the optical fiber 23 so as to face the core 23a at a distance. A lens frame 43 for holding the lens 42 is formed on the inner peripheral surface of the reflection tip body 41a. The lens frame 43 is situated on the distal end side of an engagement portion with the male screw portion 27 of the holder 24. The lens 42 may have a desired shape (a spherical lens, an aspherical lens, etc.) so as to produce a laser beam of a desired shape.

A ring-shaped projection 44 is formed between the engagement portion with the male screw portion 27 of the holder 24 and the lens frame 43. The inner peripheral surface of the projection 44 is provided with a screw hole portion 45. A lens holding ring 46 for holding the lens 42 supported by the lens frame 43 is meshed with the screw hole portion 45.

As is shown in FIG. 11B, the inner peripheral surface of the reflection tip body 41a is provided with a through-hole 47 penetrating the projection 44 and lens frame 43. Passage of a cooling fluid between the front and rear sides of the lens 42 is ensured by the through-hole 47.

Laser beams of desired shapes, which are suitable for various objects for medical treatment, can be obtained by changing the shape of the reflection surface 48 of the reflection tip body 41a.

The operation of the ninth embodiment with the above structure will now be described. In the ninth embodiment, as shown in FIG. 11A, the lens of the reflection tip 41 is a concave lens and the reflection surface 48 is a concave surface.

At the time of the laser medical treatment, a laser beam is emitted from the core 23a of the optical fiber 23 of laser probe 21 and is enlarged by the concave lens 42. Then, the enlarged beam is converged by the laser beam reflection surface 48 of the reflection tip body 41a and emitted from the laser beam output port 50 of reflection tip body 41a in the lateral direction of the laser probe 21.

A fluid flowing through the fluid passage 26 between the optical fiber 23 and outer tube 22 passes through the slits 25 of the holder 24 and the through-hole 47 penetrating the projection 44 and lens frame 43 provided on the inner peripheral surface of the reflection tip body 41a. Further, the fluid flows through the laser beam input port 49 of the reflection tip body 41a and is discharged from the laser beam output port 50 of the reflection tip body 41a.

The ninth embodiment having the above structure has the following advantages. Since the laser beam emitted from the core 23a of optical fiber 23 of the laser probe 21 is enlarged by the concave lens 42, the enlarged beam is radiated on the laser beam reflection surface 48 of the reflection tip body 41a. Thus, the power density of the laser beam radiated on the laser beam reflection surface 48 of the reflection tip body 41a is lower than in the case where the concave lens 42 is not provided. Accordingly, the peak value of the generated heat distribution on the laser beam reflection surface 48 lowers and burning of the reflection surface 48 can be prevented.

In addition, since the laser beam reflection surface 48 of the reflection tip body 41a is a concave surface with a substantially arcuated cross section, the laser beam is guided to the area for radiation in a converging manner. Accordingly, a high laser power density can be obtained at the area for radiation.

FIG. 12A shows a rotational adjustment unit 61 of the laser probe 21 of, e.g. the first embodiment. The laser probe 21 is passed twice through a probe holder 62 constituted by a tube of, e.g. silicone rubber, thus forming a loop section 63. The inside diameter of the probe holder 62 constituted by the tube is set so that the laser probe 21 may be passed through the probe holder 62 twice.

The laser probe 21 with the above structure is used in combination with the urethroscope 1, as shown in FIG. 12B. The direction of laser radiation by the laser probe 21 is adjusted by rotation, the probe holder 62 is held by the fingers and rotated in the direction of the arrow in FIG. 12A. In this case, since the loop section 63, too, rotates around the probe holder 62, the reflection tip 28 at the distal end of the laser probe 21 rotates by the same degree. Thus, the direction of laser radiation of the laser probe 21 can be adjusted by rotation.

With the above simple structure wherein the laser probe 21 is passed twice through the probe holder 62 constituted by the tube of, e.g. silicone rubber and the loop section 63 is formed, rotational idling between the holder 24 and outer tube 22 of the laser probe 21 can be prevented and the outer tube 22 and optical fiber 23 of the laser probe 21 can be surely rotated as one body.

If the diameter of the loop section 63 is decreased excessively, the laser beam may leak from the optical fiber 23 or the optical fiber 23 may break. It is desirable, therefore, that the diameter of the loop section 63 be set at about 4 cm or more.

With the above structure, even if the outer tube 22 and holder 24 of the laser probe 21 are constructed axially immovable and irremovable but rotatable, as shown in FIG. 1, the holder 24 and reflection tip body 28a can be surely rotated when the probe holder 62 is rotated. Thus, there is no concern that the direction of laser beam radiation cannot be adjusted by rotation owing to rotational idling between the outer tube 22 and holder 24.

By rotating the outer tube 22 by using the rotational adjustment unit 61 at a location apart from the connecting portion between the outer tube 22 and holder 24, a torque can be exactly transmitted to the connecting portion between the outer tube 22 and holder 24 and the reflection tip body 28a can be rotated. If the outer tube 22 is held and rotated at a location apart from the connecting portion between the outer tube 22 and holder 24 with the rotational adjustment unit 61 being not used, a torque is not smoothly transmitted to the connecting portion between the outer tube 22 and holder 24 and the reflection tip body 28a may not be rotated. This undesirable situation can be avoided in the present embodiment.

In the case where a grip 71 constituted by a tube of, e.g. silicone rubber is fixed on the outer peripheral surface of the laser probe 21 and the laser probe 21 is adjusted by rotation by means of the grip 71, as shown in FIG. 13, it is necessary that a rotational adjustment part for adjusting a laser beam radiation direction of the laser probe 21 be provided with a complex fixing means having a strong fixing force enough to prevent idling even if a great torque is applied. By contrast, if the rotational adjustment unit 61 as shown in FIGS. 12A and 12B is used, there is no need to provide a complex fixing means. Accordingly, a rotational adjustment unit for adjusting a laser beam radiation direction of the laser probe 21 can be formed at low cost.

Furthermore, in the case of the rotational adjustment unit 61 as shown in FIGS. 12A and 12B, it is not necessary that the fixing force of the grip 71, as shown in FIG. 13, for rotationally adjusting the laser probe 21 be increased. Thus, damage to the laser probe 21 can be prevented.

FIG. 14 shows a first modification of the rotational adjustment unit 61 of the laser probe 21 which is shown in FIG. 12A. In the first modification, the probe holder 62 constituted by the tube is replaced by a coil 81.

FIG. 15 shows a second modification of the rotational adjustment unit 61 of the laser probe 21 which is shown in FIG. 12A. Two holes 92 and 93 are made in a middle portion of a tube 91 of, e.g. silicone rubber. The laser probe 21 is passed through the holes 92 and 93, and the tube 91 itself is provided along the loop section 63 of the laser probe 21.

In this case, the radius R of curvature of the loop section 63 of the laser probe 21 can be set at a predetermined value by determining the length of the tube 91. It is possible, therefore, to prevent the radius R of curvature of the loop section 63 of the laser probe 21 from decreasing excessively, resulting in leakage of laser beam from the laser probe 21 or breakage of the laser probe 21.

Figure 16:
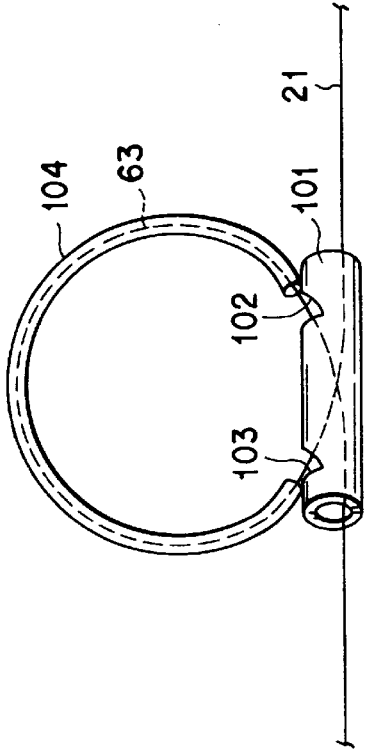
FIG. 16 is a perspective view showing a third modification of the rotational adjustment unit of the laser probe.

FIG. 16 shows a third modification of the rotational adjustment unit 61 of the laser probe 21 which is shown in FIG. 12A. Notches 102 and 103 are provided at both end portions of a tube 101. The laser probe 21 is passed through the notches 102 and 103, thereby forming a loop section 63.

Figure 17:
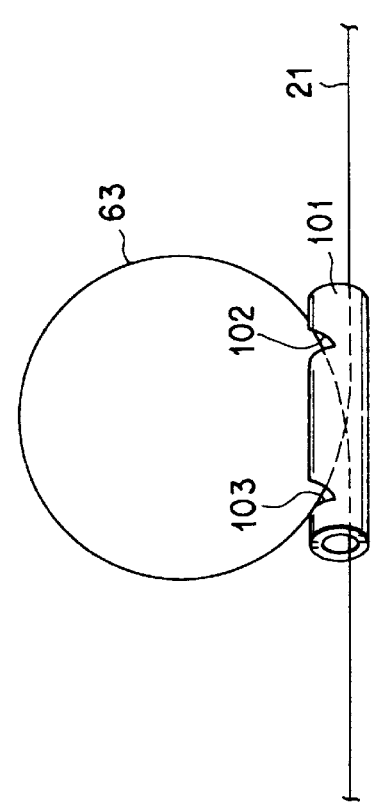
FIG. 17 is a perspective view showing a fourth modification of the rotational adjustment unit of the laser probe.

FIG. 17 shows a fourth modification of the rotational adjustment unit 61 of the laser probe 21 which is shown in FIG. 12A. Like the third modification shown in FIG. 16, notches 102 and 103 are provided at both end portions of a tube 101 and the laser probe 21 is passed through the notches 102 and 103, thereby forming a loop section 63. The loop section 63 of the laser probe 21 is inserted into another tube 104.

In this case, like the second modification shown in FIG. 15, the radius R of curvature of the loop section 63 of the laser probe 21 can be set at a predetermined value by determining the length of the tube 101. It is possible, therefore, to prevent the radius R of curvature of the loop section 63 of the laser probe 21 from decreasing excessively, resulting in leakage of laser beam from the laser probe 21 or breakage of the laser probe 21. It should be noted that when the loop section 63 is formed, it may be merely fixed by an adhesive tape, etc.

Figure 18:
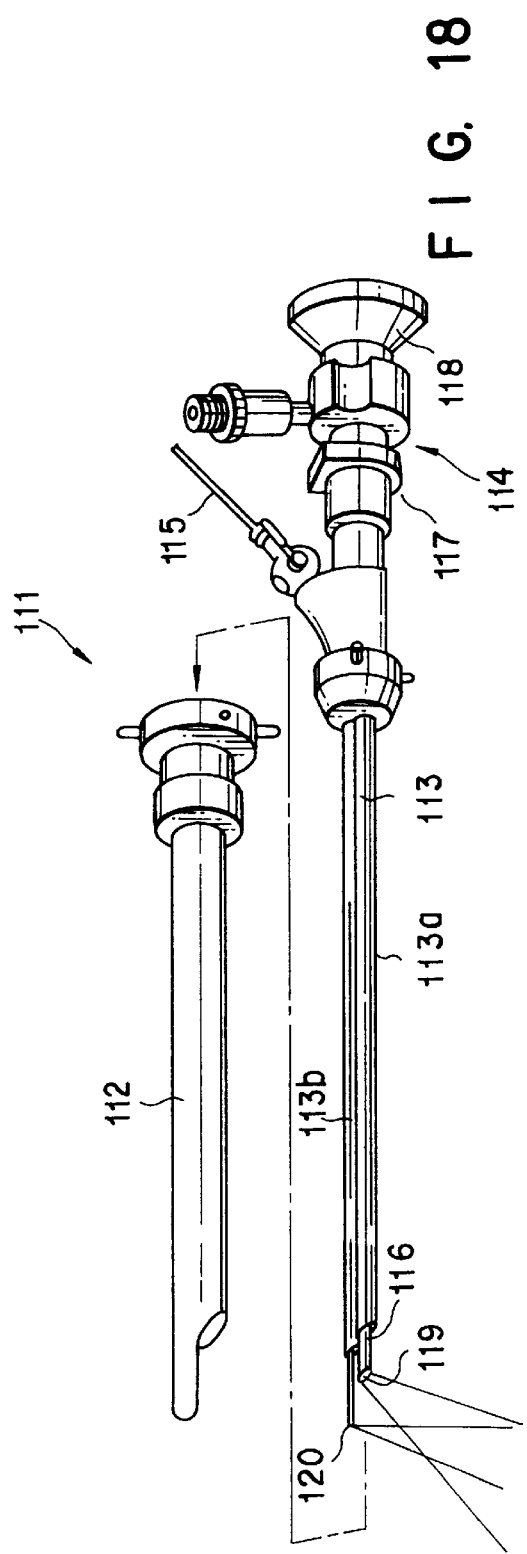
FIG. 18 is a perspective view of an urethroscope in the state in which the outer sheath is removed.

FIG. 18 shows schematically the structure of a laser medical treatment apparatus 111. Reference numeral 112 denotes an outer sheath of an urethroscope, and numeral 113 an inner sheath inserted in the outer sheath 112.

The inner sheath 113 is provided with an optical scope tube insertion portion 113a in which an optical scope tube 114 is inserted, and a forceps insertion portion 113b in which a laser probe 115, situated substantially in parallel to the optical scope tube 114, is inserted.

The optical scope tube 114 is provided with an insertion portion 116 to be inserted into the body, and a proximal structure 117 coupled to a proximal end portion of the insertion portion 116. Furthermore, the proximal structure 117 is provided with an eyepiece 118 in which an eyepiece lens is built. The insertion portion 116 of the optical scope tube 114 is inserted in the optical scope tube insertion portion 113a of the inner sheath 113.

Figure 19:
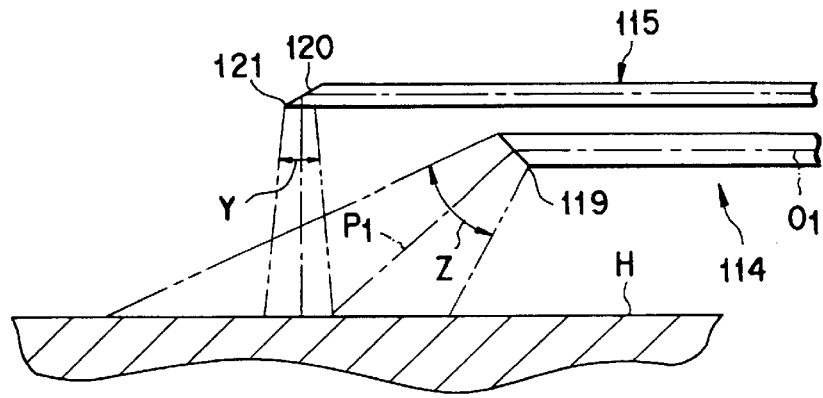
FIG. 19 shows schematically the structure of a laser medical treatment apparatus.

As is shown in FIG. 19, a distal end portion of the insertion portion 116 is provided with an observation portion 119 designed to be capable of diagonally forward observation such that a center axis P1 of an observation visual field Z of the optical scope tube 114 is inclined diagonally forward with respect to a center axis O1 of the insertion portion 116. An observation image incident on the observation portion 119 is transmitted to the eyepiece 118 via an image transmission medium of, e.g. an optical fiber within the insertion portion 116. In FIG. 19, symbol H denotes a tubular cavity wall of a tubular cavity organ at which an affected part of, e.g. prostatomegaly (BPH) is formed. The forceps insertion portion 113b of the inner sheath 113 is situated at a location opposite to the direction of the diagonal view of the observation visual field Z of the optical scope tube 114 inserted in the optical scope tube insertion portion 113a.

A proximal end portion of the laser probe 115 is connected to a laser apparatus (not shown) for emitting a laser beam. A distal end portion of the laser probe 115 is extended in front of the observation portion 119 of the optical scope tube 114. Moreover, the distal end portion of the laser probe 115 is provided with a laser beam emission portion 120 situated outside the visual field Z of the optical scope tube 114.

Figure 20:
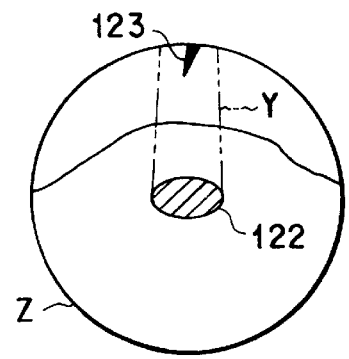
FIG. 20 is a plan view showing an observed image in a visual field of an optical scope tube.

The laser beam emission portion 120 is provided with a laser beam reflection surface (laser beam guide means) 121 formed by cutting the distal end portion of the laser probe 115 diagonally. A laser beam sent from the laser apparatus (not shown) through the laser probe 115 is reflected laterally by the laser beam reflection surface 121 of the emission portion 120. The reflected beam is guided to a radiation area 122 within the visual field Z of the optical scope tube 114, as shown in FIG. 20. In FIG. 20, reference symbol Y denotes a laser beam radiation range, and 123 a mark of the observation visual field Z of the eyepiece 118 of the optical visual tube 114. The laser probe 115 is supported movably in the axial direction thereof. The distal end portion of the laser probe 115 can be adjustably situated at such a position where the laser beam reflected laterally from the laser beam reflection surface 121 is radiated at a substantially center of the visual field Z of the optical scope tube 114.

The operation of the above structure will now be described. At the time of laser medical treatment, the insertion portion of the urethroscope is inserted into the body via the urethra in the state in which the optical scope tube 114 and laser probe 115 are inserted in the inner sheath 113 of the urethroscope and the inner sheath 113 is covered with the outer sheath 112. In this case, the distal end portion of the laser probe 115 is extended in front of the observation portion 119 of the optical scope tube 114. Since the laser beam emission portion 120 at the distal end portion of the laser probe 115 is situated outside the visual field Z of the optical scope tube 114, the distal end portion of the laser probe 115 is not present in the visual field Z of the optical scope tube 114 and the entire visual field Z of the optical scope tube 114 can be observed.

When the distal end portion of the urethroscope inserted into the body has reached the affected part of the BPH, a visible guide beam for confirming the radiation area 122 is emitted from the laser probe 115. The laser probe 115 is adjusted in the axial direction thereof so that the guide beam emitted from the laser probe 115 is radiated substantially at the center of the visual field Z of the optical scope tube 114.

After the adjustment, the laser beam is radiated from the laser probe 115 to the radiation area 122. In this case, the laser beam sent through the laser probe 115 is reflected by the laser beam reflection surface 121 at the distal end of the laser probe 115. The reflected beam is radiated laterally from the laser probe 115 and applied to the radiation area 122 located substantially at the center of the visual field Z of the optical scope tube 114. In the case of merely heating the radiation area, the laser beam is emitted at low power. In the case of coagulation and transpiration, the laser beam is emitted at high power.

As the laser beam radiation is continued, the temperature of the radiation area 122 rises and the radiation area 122 is whitened. Then, the radiation area 122 is coagulated. In this case, if the laser beam is radiated at high power, the body tissue is transpirated and a crater is formed at the prostate tissue.

The prostate tissue irradiated with the laser beam is necrotized and removed so that the prostate tubular cavity is enlarged. Thereby, the decrease in amount of urine or stop of urine, which is a condition of BPH, is healed.

With the above structure, at the time of laser medical treatment, the laser beam emitted from the emission portion of the laser probe 115 situated outside the visual field Z of the optical scope tube 114 is guided by the laser beam reflection surface 121 towards the radiation area 122 within the visual field Z of the optical scope tube 114. Thus, the entire visual field Z of the optical scope tube 114 can be observed. In the prior art, part of the visual field Z of the optical scope tube 114 is shielded by the distal end portion of the laser probe 115 extended to the visual field Z of the optical scope tube 114. This undesirable situation is avoided in the above structure. Thus, the radiation area 122 irradiated with the laser beam from the emission portion 120 of the laser probe 115 can be directly observed by the naked eye within the visual field Z of the optical scope tube 114, and the laser medical treatment can be performed safely and exactly.

Figure 21:
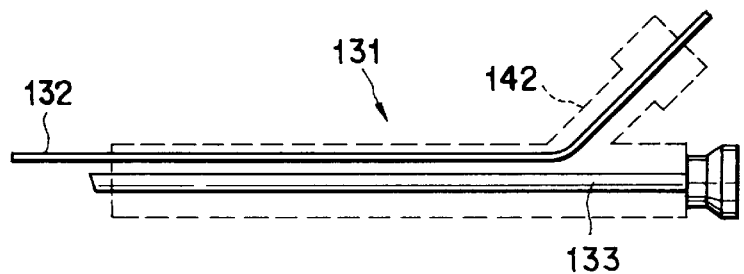
FIG. 21 shows schematically the structure of a main portion of a solid scope as combined with the laser scope.
Figure 22:
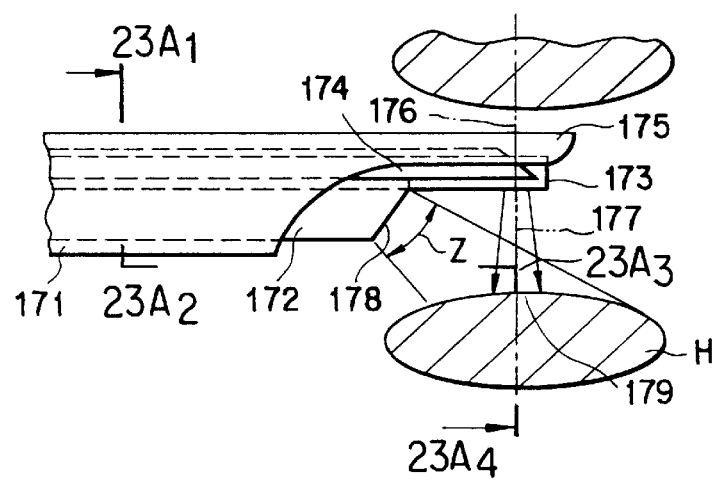
FIG. 22 is a vertical cross-sectional view showing schematically the structure of a main portion of a modification of the laser medical treatment apparatus.

FIG. 21 shows a combination of a hard scope 131 and a laser probe 132. Reference numeral 133 denotes an optical scope tube of the hard scope 131. FIGS. 22 and 23A show schematically the structure of a main part of a modification of the laser medical treatment apparatus. This modification relates to a composite function type small-sized laser medical treatment apparatus wherein a laser medical treatment apparatus in which an endoscope and a laser probe are combined is further combined with an ultrasonic diagnosis mechanism for performing a diagnosis in the depth direction of an affected part. In this case, when the prostate is treated, the surface of the affected part can be observed by the endoscope and the affected part can be diagnosed by ultrasonic waves. At the same time, medical treatment by means of a laser beam can be performed.

As is shown in FIG. 22, in the laser medical treatment apparatus according to the present modification, an optical scope tube 172 capable of diagonally forward observation, an ultrasonic probe 173 and a laser probe 174 are inserted in a sheath 171 capable of being inserted into the prostate. A distal end portion of the sheath 171 is provided with a beak-like tip portion 175 formed by partly cutting a peripheral surface of a cylindrical body of the sheath 171.

The ultrasonic probe 173 can perform a diagnosis in a cross section in the direction of extension of the ultrasonic probe 173, i.e. in a cross section substantially perpendicular to the axis of the sheath 171. Furthermore, the laser probe 174 can radiate a laser beam in a lateral direction (90° to the axis of the sheath 171). The direction of a diagnosis plane 176 of the ultrasonic probe 173 coincides with a laser beam emission axis 177 of the laser probe 174.

The distal end portion of the optical scope tube 172 of the diagonally forward observation type is situated behind the distal end portion of the ultrasonic probe 173. In this case, the center axis of the visual field Z of the optical scope tube 172 is inclined diagonally downwards in the forward direction in FIG. 22 with respect to the axis of the sheath 171. Thus, an observation portion 178 capable of diagonally forward observation is formed. The laser probe 174 and ultrasonic probe 173 within the sheath 171 are situated at a position opposite to the direction of diagonal observation of the observation visual field Z of the optical scope tube 172. A laser beam emitted from a laser apparatus (not shown) via the laser probe 174 is radiated laterally from the distal end portion of the laser probe 174 and guided to a radiation area 179 within the visual field of the optical scope tube 172.

FIG. 23A is a cross-sectional view taken along line 23A$_1$–23A$_2$–23A$_3$–23A$_4$ in FIG. 22. A gap within the sheath 171 serves as a passage for physiological saline for circulation.

The operation of the above structure will now be described. At the time of laser medical treatment, the sheath 171 of the urethroscope is inserted into the prostate cavity via the urethra in the state in which the ultrasonic probe 173, laser probe 174 and optical scope tube 172 are inserted into the sheath 171.

When the distal end portion of the urethroscope has been inserted to a target area within the prostate cavity, the condition of the surface of an affected part I of a prostate tissue H is observed on the basis of an endoscopic image obtained by the optical scope tube 172. Further, a tomographic image is obtained by the ultrasonic probe 173 in an area substantially at the center of the visual field Z of the optical scope tube 172 of the endoscope. Based on the tomographic image, the condition of the affected part I of prostate tissue H in the depth direction can be observed.

While the surface of the affected part I is being observed by the optical scope tube 172 and the affected part I is being diagnosed in the depth direction by the ultrasonic probe 173, the laser beam is emitted from the laser probe 174. At this time, the laser beam is radiated on the affected part I of prostate tissue H on the plane of ultrasonic diagnosis. As is shown in FIG. 23A, the affected part I of prostate tissue H is heated, coagulated or transpired by laser beam radiation and is thus deformed.

FIG. 23B shows an ultrasonic diagnosis image obtained by the ultrasonic probe 173 at this time. In the ultrasonic diagnosis image, symbol W denotes a substantially semicircular ultrasonic diagnosis range, H$_1$ denotes an ultrasonic image of the prostate tissue H, and I$_1$ denotes an ultrasonic image of a part coagulated and deformed by laser beam radiation. Accordingly, the condition of transformation of the prostate tissue H in the depth direction due to laser beam radiation can be confirmed in real time by the ultrasonic diagnosis image.

FIG. 23C shows an endoscopic image obtained by the optical scope tube 172 at this time. Based on the endoscopic image, the condition of the surface of the affected part I of prostate tissue H can be observed. At this time, since the distal end portion of the laser probe 174 is situated outside the visual field Z of the optical scope tube 172, the distal end portion of the laser probe 174 does not shield part of the observation visual field Z of the optical scope tube 172.

With the above structure, too, when the laser medical treatment is performed, the laser beam emitted from the emission end portion of the laser probe 174 situated outside the visual field Z of the optical scope tube 172 is guided to the radiation area 179 within the visual field Z of the optical scope tube 172. Thus, unlike the prior art, part of the visual field Z of the optical scope tube 172 is not shielded by the distal end portion of the laser probe 174 extended to the visual field Z of the optical scope tube 172. Therefore, like the first embodiment, the radiation area 179 irradiated with the laser beam from the emission portion of the laser probe 174 can be directly observed by the naked eye within the visual field Z of the optical scope tube 172, and the laser medical treatment can be performed safely and exactly. Furthermore, according to the present embodiment, on the basis of the ultrasonic diagnosis image obtained by the ultrasonic probe 173, the condition of transformation of the prostate tissue H in the depth direction due to laser beam radiation can be confirmed in real time.

Figure 24A:
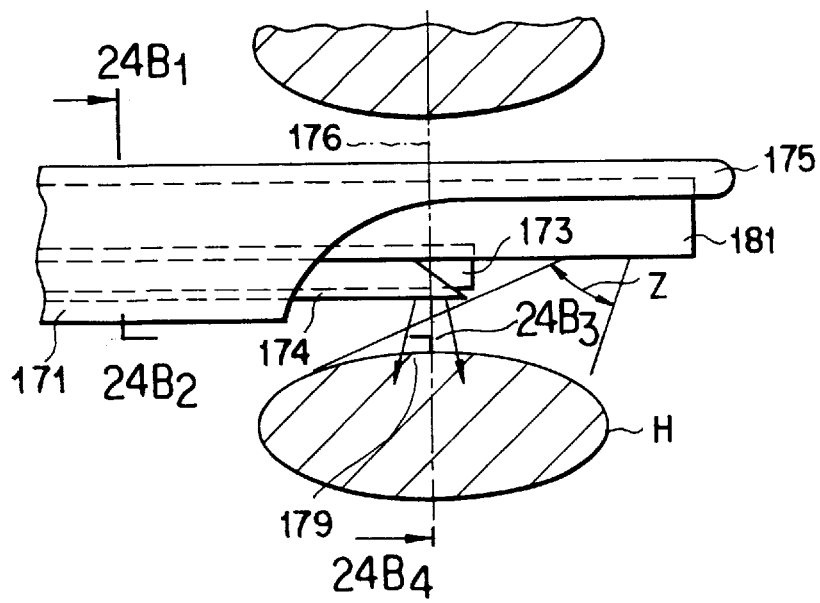
FIG. 24A is a vertical cross-sectional view showing schematically the structure of a main portion of a second modification of the laser medical treatment apparatus.
Figure 24B:
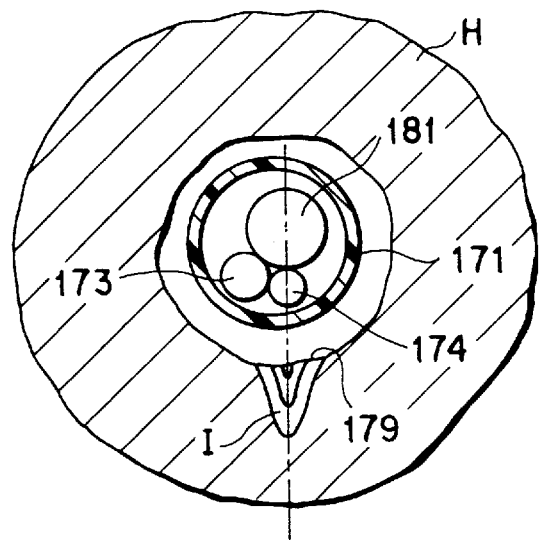
FIG. 24B is a cross-sectional view taken along line $24B_1$–$24B_2$–$24B_3$–$24B_4$ in FIG. 24A.

FIGS. 24A and 24B show schematically the structure of a main part of a second modification of the laser medical treatment apparatus. In the second modification, as shown in FIG. 24A, an optical scope tube 181 of the diagonally forward observation type is used. In this case, a distal end portion of the optical scope tube 181 is situated in front of distal end portions of the laser probe 174 and ultrasonic probe 173.

With the above structure, too, when the laser medical treatment is performed, the laser beam emitted from the emission end portion of the laser probe 174 situated outside the visual field Z of the optical scope tube 181 is guided to the radiation area 179 within the visual field Z of the optical scope tube 181. Thus, the entire visual field Z of the optical scope tube 181 can be visually observed and the same advantages as with the aforementioned laser medical treatment apparatus can be obtained. Even if the distal end portion of the laser probe is viewed above within the visual field, the visual field is hardly shielded and there is no problem.

Additional advantages and modifications will readily occur to those skilled in the art. Therefore, the invention in its broader aspects is not limited to the specific details, and representative devices shown and described herein. Accordingly, various modifications may be made without departing from the spirit or scope of the general inventive concept as defined by the appended claims and their equivalents.

What is claimed is:

1. A laser probe comprising:
   an optical fiber for guiding a laser beam;
   a tube in which the optical fiber is inserted;
   a holder for fixing the optical fiber and an end portion of the tube where the laser beam is emitted; and
   a reflection tip detachably attached to the holder and having a reflection surface for reflecting the laser beam emitted from the optical fiber, the reflection surface reflecting the laser beam along a laser optical path; and
   a lens positioned in said reflection tip between said optical fiber and said reflection surface, and in a path of said laser beam as it is emitted from said optical fiber;
   wherein:
      said holder includes a slit portion,
      a cooling fluid passage is defined by a space between the optical fiber and the tube, and
      the cooling fluid passage extends through the slit portion of said holder, through said space, and opens at an emission end portion of the optical fiber in the vicinity of the reflection surface of the reflection tip, such that cooling fluid flows through said fluid passage to contact said reflection surface, and flows along the laser optical path after contacting the reflection surface, whereby said cooling fluid passage communicates a fluid to outside of the reflection tip.

2. The laser probe according to claim 1, wherein said reflection tip is detachably attached to the holder by means of a screw thread.

3. The laser probe according to claim 2, wherein said reflection tip is provided with a male screw thread and said holder is provided with a female screw thread.

4. The laser probe according to claim 3, wherein an outer surface of a first end portion of said reflection tip is provided with a male screw thread, an outer surface of a second end portion of said reflection tip is formed in a spherical shape, a space is provided between said first end portion and said second end portion of the reflection tip, a laser beam reflection surface is provided on a side of the space opposite to the side at which the male screw thread is provided, and there is provided an internal cavity communicating between an end portion of said male screw thread and said space.

5. The laser probe according to claim 1, wherein said reflection tip is provided with a female screw thread and said holder is provided with a male screw thread.

6. The laser probe according to claim 5, wherein an inner surface of a first end portion of said reflection tip is provided with a female screw thread, an outer surface of a second end portion of said reflection tip is formed in a spherical shape, a space is provided between said first end portion and said second end portion of the reflection tip, and a laser beam reflection surface is provided on a side of the space opposite to the side at which the female screw thread is provided.

7. The laser probe according o claim 1, wherein said reflection surface of the reflection tip comprises a flat surface.

8. The laser probe according to claim 7, wherein said reflection surface of the reflection tip is inclined about 30° to 70° with respect to an axis of the reflection tip.

9. The laser probe according to claim 1, wherein said reflection surface comprises one of a concave curved surface and a convex curved surface.

10. The laser probe according to claim 9, wherein a radius of the reflection surface is 1 to 3 mm.

11. The laser probe according to claim 9, wherein the reflection surface of the reflection tip is shaped to reflect the laser beam such that the reflected laser beam is diverged only in one direction.

12. The laser probe according to claim 1, wherein said reflection surface comprises a substantially concave surface, the laser beam reflected by said reflection surface being most focused at a point located in the vicinity of one of an outer peripheral surface of the reflection tip and inside said outer peripheral surface.

13. The laser probe according to claim 1, wherein said reflection surface comprises one of a substantially concave spherical surface and a substantially convex spherical surface.

14. The laser probe according to claim 13, wherein a radius of said substantially concave and substantially convex spherical reflection surfaces is 1 to 3 mm.

15. The laser probe according to claim 13, wherein the reflection surface of the reflection tip is shaped to reflect the laser beam such that the reflected laser beam has a substantially circular cross section.

16. The laser probe according to claim 1, wherein said reflection surface comprises a substantially concave spherical surface, the laser beam reflected by said reflection surface being most focused at a point located in the vicinity of one of an outer peripheral surface of the reflection tip and inside said outer peripheral surface.

17. The laser probe according to claim 1, wherein a space defined between first and second end portions of the reflection tip is open in a direction lateral to a longitudinal axis of the laser probe and wherein the laser beam is reflected in the lateral direction.

18. The laser probe according to claim 1, wherein an outside diameter of the laser probe is 3 mm or less.

19. The laser probe according to claim 1, wherein said reflection tip comprises a metallic material, and at least said reflection surface is subjected to at least one of buffing and chemical polishing.

20. The laser probe according to claim 1, wherein said reflection tip is made of a metallic material, wherein at least said reflection surface is subjected to at least one of buffing and chemical polishing, and wherein at least said reflection surface is then subjected to plating with one of gold and platinum.

21. The laser probe according to claim 1, wherein the reflection surface of the reflection tip is shaped to reflect the laser beam such that the laser beam has a greater cross-sectional area after the laser beam is reflected by said reflection surface than before the laser beam is reflected by said reflection surface.

22. The laser probe according to claim 1, wherein the reflection surface of the reflection tip is shaped to reflect the laser beam such that a divergence angle of the laser beam emitted from the optical fiber and reflected by the reflecting surface is increased from a range of 5° to 30° to a range of 10° to 100°.

23. The laser probe according to claim 1, wherein the reflection surface of the reflection tip is shaped to reflect the laser beam such that the laser beam is once converged and then diverged at a greater divergence angle than before the laser beam is reflected.

24. The laser probe according to claim 1, wherein the reflection surface of the reflection tip is shaped to reflect the laser beam such that the reflected laser beam has one of a substantially overall cross section and a substantially rectangular cross section.

25. The laser probe according to claim 1, wherein the reflection surface reflects the laser beam with a different widening angle in accordance with different reflection directions.

26. The laser probe according to claim 1, wherein the reflection surface of the reflection tip is shaped to reflect the laser beam such that a cross-section of the reflected laser beam has a longitudinal axis which is parallel to a longitudinal axis of the laser probe.

27. The laser probe according to claim 1, wherein the reflection surface of the reflection tip is shaped to reflect the laser beam such that a longitudinal axis of the reflected laser beam is parallel to a transverse axis of the laser probe.

28. The laser probe according to claim 1, wherein the reflection surface of the reflection tip is shaped to reflect the laser beam such that a divergence angle of the laser beam after being reflected reflection is substantially equal to or less than a divergence angle of the laser beam before being reflected.

29. The laser probe according to claim 1, wherein a diameter of the reflection tip is substantially equal to a diameter of the tube.

30. The laser probe according to claim 1, wherein said fluid passage is coupled to fluid supply means for supplying the fluid.

31. The laser probe according to claim 1, wherein the fluid passage is arranged to pass the fluid over the reflection surface and discharge the fluid outside of the reflection tip to thereby decrease a temperature of the reflection tip.

32. The laser probe according to claim 1, wherein the fluid passage is arranged to pass the fluid over the reflection surface and discharge the fluid outside of the reflection tip to remove air bubbles from the reflection surface of the reflection tip, thereby preventing burning of the reflection surface.

33. The laser probe according to claim 1, wherein the fluid passage is arranged to pass the fluid over the reflection-surface and discharge the fluid outside of the reflection tip to remove tissue, blood and air bubbles from an emission end of the optical fiber and the reflection surface, to thereby efficiently enable the laser beam to be guided.

34. The laser probe according to claim 1, wherein the fluid passage is arranged to pass the fluid over the reflection surface, discharge the fluid outside of the reflection tip and direct the fluid to a tissue, to thereby cool a surface of the tissue.

35. The laser probe according to claim 1, wherein the fluid passage is arranged to have 5 to 100 cc/minute of water flow therein.

36. A laser probe according to claim 1, wherein said tube is an inner sheath of an endoscope.

37. The laser probe according to claim 36, wherein said endoscope is of a continuous irrigation type wherein a fluid discharge passage for discharging fluid is defined between the inner sheath and an outer sheath of the endoscope, and fluid is continuously supplied and discharged through said cooling fluid passage and said fluid discharge passage simultaneously.

38. A laser probe comprising:

an optical fiber for guiding a laser beam;

a tube in which the optical fiber is inserted;

a holder for fixing the optical fiber and an end portion of the tube where the laser beam is emitted; and a reflection tip detachably attached to the holder and having a reflection surface for reflecting the laser beam emitted from the optical fiber, wherein a fluid passage is defined by a space between the optical fiber and the tube for supplying the reflection surface of the reflection tip with a fluid, and wherein said laser probe includes holding means for holding, in a loop shape, a portion of the tube and the optical fiber inserted therein, wherein said loop-shaped portion of the laser probe is rotated to rotate a distal end portion of the laser probe such that the tube and the optical fiber inserted therein are rotated as one body.

39. A laser probe comprising:

an optical fiber for guiding a laser beam;

a tube in which the optical fiber is inserted;

a holder for fixing the optical fiber and an end portion of the tube where the laser beam is emitted; and a reflection tip detachably attached to the holder and having a reflection surface for reflecting the laser beam emitted from the optical fiber, wherein said holder includes a slit portion, wherein a fluid passage is defined by a space between the optical fiber and the tube, and wherein the fluid passage extends through the slit portion of said holder and opens at an emission end portion of the optical fiber in the vicinity of the reflection surface of the reflection tip, said fluid passage communicating a fluid to outside of the reflection tip, and wherein said laser probe includes holding means for holding, in a loop shape, a portion of the tube and the optical fiber inserted therein, wherein said loop-shaped portion of the laser probe is rotated to rotate a distal end portion of the laser probe such that the tube and the optical fiber inserted therein are rotated as one body.

* * * * *